(12) United States Patent
Chan et al.

(10) Patent No.: US 8,263,758 B2
(45) Date of Patent: *Sep. 11, 2012

(54) LEAF-SPECIFIC CHLOROPHYLL A/B BINDING PROTEIN GENE PROMOTER FROM OIL PALM

(75) Inventors: Pek Lan Chan, Selangor (MY); Siti Nor Akmar Abdullah, Selangor (MY)

(73) Assignee: Malaysian Palm Oil Board, Kajang, Selangor Darul Ehsan (MY)

( * ) Notice: Subject to any disclaimer, the term of this patent is extended or adjusted under 35 U.S.C. 154(b) by 373 days.

This patent is subject to a terminal disclaimer.

(21) Appl. No.: 12/632,321

(22) Filed: Dec. 7, 2009

(65) Prior Publication Data
US 2010/0088786 A1   Apr. 8, 2010

Related U.S. Application Data

(63) Continuation of application No. 11/452,065, filed on Jun. 13, 2006, now Pat. No. 7,629,454.

(30) Foreign Application Priority Data

Jun. 13, 2005 (MY) .............................. PI 20052661

(51) Int. Cl.
C07H 21/04 (2006.01)
C12N 15/82 (2006.01)
A01H 5/00 (2006.01)
(52) U.S. Cl. ....... 536/24.1; 800/287; 800/278; 800/298; 435/320.1; 435/468; 435/419
(58) Field of Classification Search .......................... None
See application file for complete search history.

(56) References Cited

U.S. PATENT DOCUMENTS 7,629,454 B2 * 12/2009 Chan et al. .................... 536/24.1
2006/0288439 A1   12/2006 Chan et al.

OTHER PUBLICATIONS

Anderson, D.M., Hudspeth, R.L., Hobbs, S.L. & Grula, J.W. 1993. Chlorophyll a/b binding protein gene expression in cotton. *Plant Physiol*. 102: 1047-1048.
Aoki, T. et al., "Variation of alkaloid productivity among several clones of hairy roots and regenerated plants of *Atropa belladonna* transformed with *Agrobacterium rhizogenes* 15834," *Plant Cell Reports* 1997; 16:282-286.
Arguello-Astorga, G. & Herrera-Estrella, L. 1998. Evolution of light-regulated plant promoters. *Annu. Rev. Plant Physiol. Plant Mol. Biol.* 49:525-555.
Benfey et al. 1990. The cauliflower mosaic virus 35S promoter: combanitorial regulation of transcription in plants. *Science* 250:959-966.
Buetow, D.E., Chen, H., Erdos, G. & Lee, S.H.Y. 1988. Regulation and expression of the multigene family coding light-harvesting chlorophyll a/b binding proteins of photosystem 11. Dlm. Govindjee et al.
(Eds). *Molecular Biology of Photosynthesis*, hlm. 283-319. New York: Kluwer Academic Publishers.
Chinn, E., Silverthorne, J. & Hohtola, A. 1995. Light-regulated and organ-specific expression of types 1, 2, and 3 light-harvesting complex b mRNAs in *Ginkgo biloba*. *Plant Physiol*. 107:593-602.
Chowdhury, M.K.U., Parveez, G.K.A. & Norihan, M.S. 1997. Evaluation of five promoters for use in transformation of oil palm (*Elaeis guineensis Jacq.*). *Plant Cell Reports*. 16:277-281.
Clough, S.J. & Bent, A.F. 1998. Floral dip: a simplified method for *Agrobacterium*-mediated transformation of *Arabidopsis thaliana*. *Plant J*. 16(6):735-743.
Demmin, D.S., Stockinger, E.J., Chang, Y.C. & Walling, L.L. 1989. Phylogenetic relationships between the chlorophyll a/b binding protein (CAB) multigene family: an intra and interspecies study. *J Mol. Evol*. 29:266-279.
Donald et al. 1990. Mutation of either G box sequences profoundly affects expression from the Arabidopsis rbcS-1A promoter. *The Embo J*. 9:1717-1726.
Doyle, J.J. & Doyle, J.L. 1990. Isolation of plant DNA from fresh tissue. FOCUS 12(1):13-15. Fernandez, S.V., Cerdan, P.D. & Staneloni, R.J. 1995. Isolation and characterization of a cluster containing six *Lhcb* I gene from potato (*Solanum tuberosum*). *Plant Physiol*. 108:1342.
Fernandez, S.V. et al., "Isolation and characterization of a cluster containing six Lhcb 1 genes from potato (*solanum tuberosum*) (GenBank accession Nos. U21111, U21112, U21113, U21114, U21115 and U20983)," *Plant Physiol*. 108:1342, 1995.
Jansson, S. & Gustafsson, P. 1990. Type I and Type 11 genes for the chlorophyll a/b-binding protein in the gymnosperm *Pinus sylvestris* (Scots pine): cDNA cloning and sequence analysis. *Plant Mol. Biol.* 14:287-296.
Jefferson, R.A., Kavanagh, T.A. and Bevan, M.V. 1987. GUS fusions: glucuronidase as a sensitive and versatile gene fusion marker in higher plants. *Embo J* 6(13):3091-3097.
Joshi, C.P. 1987. An inspection of the domain between putative TATA box and translation start site in 79 plant genes. *Nucleic Acids Res.* 15(16):6643-6653.
Kehoe, D.M., Degenhardt, J., Winicov, 1. & Tobin, E.M. 1994. Two 10 bp regions are critical for phytochrome regulation of a *Lemna gibba Lhcb* gene promoter. *Plant Cell* 6:1123-1134.
Kim et al. 1994. A 20 nucleotide upstream element is essential for the nopaline synthase (nos) promoter activity. *Plant Mol. Biol.* 24:105-117.

(Continued)

*Primary Examiner* — Cathy Kingdon Worley
(74) *Attorney, Agent, or Firm* — Wolf, Greenfield & Sacks, P.C.

(57) ABSTRACT

The present invention discloses a promoter sequence of light-harvesting chlorophyll a/b binding protein pGWLS01 isolated from the oil palm leaf. This promoter enables the manipulation of oil palm leaves for the production of high value-added products via genetic engineering tools. The novel features of the promoter itself which regulate high and specific expression of foreign genes in the leaves will avoid the interference of novel products in the commodity oil extracted from mesocarp and kernel tissues. Furthermore, the promoter is also potentially useful in the production of insect-resistant palm.

15 Claims, 16 Drawing Sheets

OTHER PUBLICATIONS

Knight, M.E., Ray, J.A. & Schuch, W. 1992. Isolation of a gene from maize encoding a chlorophyll a/b binding protein. *Plant Mol. Biol.* 19:533-536.

Kroczek, R.A. & Siebert, E. 1990. Optimization of Northern analysis by vacuum blotting, RNA-transfer visualization, and ultraviolet fixation. *Anal. Biochem.* 184:90-95.

Matton, D.P., Prescott, G., Bertrand, C., Camirand, A. & Brisson, N. 1993. Identification of *cis*-acting elements involved in the regulation of the pathogenes is related gene STH-2 in potato. *Plant Mol. Biol.* 22:279-291.

Mayer, A., Zondag, G.B. & Hensgens, L.A.M. 2001. A simple screening method for transgenic rice tissue based on PCR. (online) http://www.gramene. org/newsletter/rice_genetics/rgn8/v8p 161.html (Jul. 20, 2003).

Mcmaster, G.K. & Carmicheal, G.G. 1977. Analysis of single- and doublestranded nucleic acids on polyacrylamide and agarose gels by using glyoxal and acridine orange. *Proc. Natl. Acad Sci. USA* 74(11):4835-4838.

Mullet, J.E. 1993. Dynamic regulation of chloroplast transcription. *Plant Physiol.* 103: 309-313.

Nakamura, M., Tsunoda, T. & Obokata, J. 2002. Photosynthesis nuclear genes generally lack TATA-boxes: a tobacco photosystem I gene responds to light through an initiator. *Plant J* 29(1):1-10.

Pastuglia, M., Roby, D., Dumas, C. & Cock, J.M. 1997. Rapid induction by wounding and bacterial infection of an S gene family receptor-like kinase gene in *Brassica oleracea*. Plant Cell 9:49-60.

Rochester, D.E., Winer, J.A. & Shah, D.M. 1986. The structure and expression of maize genes encoding the major heat shock protein, hsp70. *Embo J* 5(3): 451-458.

Sambrook, J. & Russell, D.W. 2001. pp. 2.25-2.37. In: *Molecular cloning: a laboratory manual*. Third Ed. New York: Cold Spring Harbor Press.

Siti Nor Akmar Abdullah, Farida, H.S. & Cheah, S.C. 1995. Construction of oil palm mesocarp cDNA library and the isolation of mesocarp-specific cDNA clones. Asia Pacific Journal of Molecular Biology and Biotechnology. 3(2):106-111.

Siti Nor Akmar Abdullah. 1999. Structure and regulation of stearoyl-ACP desaturase and metallothionien-like genes in developing fruits of oil palm. Ph.D Thesis. pp 40-40. U.K.: University of East Anglia.

Stockinger, E.J. & Walling, L.L. 1994. A chlorophyll a/b binding gene from soybean (*Glycine max*[L.] Merr.). *Plant Physiol.* 104:1475-1476.

Weigel, D. & Glazebrook, J. 2002. pp. 119-141. In: *Arabidopsis: a laboratory manual*. Cold Spring Harbor Laboratory Press, Cold Spring Harbor, New York.

\* cited by examiner

FIGURE 1

```
          A  D  P  E  T  F  A  K  N  R  E  L  E  V  I  R  C  R  W  A
  2   gctgatccggagaccttcgccaagaaccgtgagctcgaggtcatccactgccgttgggcc   61
          M  L  G  A  L  G  C  V  F  P  E  L  L  A  R  N  G  V  K  F
  62  atgctcggcgctcttggctgcgtcttcccggagcttctcgcacgaaacggcgtcaagttc   121
          G  E  A  V  W  F  K  A  G  A  Q  I  F  S  E  G  G  L  D  Y
 122  ggcgaggccgtctggttcaaaggtggtgcccagatctttagtgagggtggtctggactac   181
          L  G  N  P  S  L  I  H  A  Q  S  I  L  A  I  W  A  C  Q  V
 182  ttgggcaaccccagcctgatccacgctcagagcattctggccatctgggcctgccaagtt   241
          V  L  M  G  A  V  E  G  Y  R  V  A  G  S  F  L  G  E  V  T
 242  gtattgatgggcgccgtcgaggggtaccgcgtcgccggtggccgctaggtgaggtcacc   301
          D  P  L  Y  P  G  G  S  F  D  P  L  G  L  A  D  D  P  E  A
 302  gacccgctgtatccgggtgggagcttcgatcccttggggttggccgatgacccggaggct   361
          F  A  K  L  K  V  K  E  I  K  N  G  R  L  A  M  F  S  M  F
 362  ttcgcagaacttaaagtgaaggagatcaagaacggcagactggccatgttctccatgttc   421
          G  F  F  V  Q  A  I  Y  P  S  K  G  P  L  E  N  L  A  D  H
 422  gggttcttcgttcaggctatcgtcactggcaagggtccgttggagaacttggccgaccac   481
          I  A  D  P
 482  atcgcggacccag   494
```

FIGURE 2

```
pLS01     ----------------------------------------------------------------
pETLS01   ADPFTFAKNRELEVIRCRNAMLGALGCVFPELLARGVFFGEAVWFYAGAQIFSEGGELGY
```

```
pLS01     ------------------------------------------TPFDPLELARDPEA
pETLS01   LGNFSLIHAQSILAIWACQVVLMGAVEGTRVAGGPLGEVTDPLYPGGSFFPLELARDPEA
                                                    ************
```

```
pLS01     FARLKVKEIKNGALAMFGMFGFFVQRIVTGKGFLENLADHLADPVRNARAYAIRPVPGK
pETLS01   FARLKVKEIKNGALAMFGMFGFFVQRIVTGKGFLENLADHLADP--------------
          ********************************************  ***
```

```
1                                              AGAGCACCTACCCAACAG   18

19   CATTTCCATTGGGATCACCGCTCCCATCTCCAAGGCATCATCTCTATCTAGTCCTTCTCA   78

M  A  A  T  M  A  L  S  S  P  S  L  A  G  K  A  V  K  L  A
79   ATGGCTGCCACCATGGCCCTCTCCTCCCCTTCCCTCGCCGGAAAAGCGGTGAAGCTCGCT  138

P  S  A  S  P  I  L  G  N  G  R  V  T  [M] R  K  T  S  T  K
139  CCCTCGGCCTCTCCCATCCTCGGGAATGGCAGGGTCACCATGCGGAAGACCTCGACCAAG  198

R  V  P  S  G  S  P  W  Y  G  P  D  R  V  K  Y  L  G  P  L
199  CGCGTCCCCTCCGGCAGCCCATGGTACGGGCCAGACCGTGTCAAGTACCTCGGCCCCTTG  258

S  G  E  P  P  S  Y  L  T  G  E  F  P  G  D  Y  G  W  D  T
259  TCTGGGGAGCCCCCGTCCTACCTGACCGGTGAATTCCCCGGTGACTATGGGTGGGACACT  318

A  G  L  S  A  D  P  E  T  F  A  K  N  R  E  L  E  V  I  H
319  GCTGGTCTCTCGGCCGACCCTGAGACCTTCGCCAAGAACCGGGAGCTCGAGGTCATCCAC  378

C  R  W  A  M  L  G  A  L  G  C  V  F  P  E  L  L  A  R  N
379  TGCAGGTGGGCCATGCTGGGTGCCCTCGGCTGCGTCTTTCCGGAGTTGCTTGCCCGCAAT  438

G  V  K  F  G  E  A  V  W  F  K  A  G  A  Q  I  F  S  E  G
439  GGCGTCAAGTTCGGCGAGGCCGTCTGGTTCAAAGCGGGAGCTCAGATCTTCAGCGAGGGC  498

G  L  D  Y  L  G  N  P  S  L  I  H  A  Q  S  I  L  A  I  W
499  GGTCTGGACTACCTGGGCAACCCGAGCTTGATCCATGCTCAGAGCATTCTGGCCATCTGG  558

A  C  Q  V  I  L  M  G  A  V  E  G  Y  R  V  A  G  G  P  L
559  GCTTGCCAAGTTATACTGATGGGTGCCGTCGAAGGGTACCGCGTCGCCGGCGGTCCCCTG  618

G  E  V  T  D  P  L  Y  P  G  G  S  F  D  P  L  G  L  A  D
619  GGTGAGGTCACCGACCCTCTGTACCCTGGGGGGAGCTTCGATCCCTTGGGCCTTGCCGAT  678

D  P  E  A  F  A  E  L  K  V  K  E  I  K  N  G  R  L  A  M
679  GACCCGGAGGCGTTCGCAGAGCTTAAAGTGAAAGAGATCAAGAACGGCAGGCTAGCCATG  738

F  S  M  F  G  F  F  V  Q  A  I  V  T  G  K  G  P  L  E  N
739  TTCTCCATGTTCGGTTTCTTTGTTCAGGCTATCGTGACCGGGAAGGGCCCGTTGGAGAAC  798

L  A  D  H  L  A  D  P  V  N  N  N  A  W  A  Y  A  T  N  F
769  CTGGCCGACCACCTTGCGGATCCTGTTAACAACAATGCTTGGGCCTACGCCACCAACTTC  858

V  P  G  K  *
859  GTGCCCGGAAAGTGAGCCTGGCAACCTTAATTAATTTGGTGCTTAGAAATTCTTCATCTG  918

919  TTGTGGTTTTTGTTTGAATTGAAATTGTTGGCGTGGTGTGCATTAAAAAAAAAAAAAAAA  978

979  AAAAA                                                         983
```

FIGURE 7

```
LS01           MAAT-MALSSPSLAGKAVKLAPSASPILGNGRVTMRKTST--KRVP-SGSPWYGPDRVKY
L.gibba        MAAS-MALSSPSLVGKAVKLAPAASEVFGEGRVSMRKTAGKPKPVS-SGSPWYGPDRVKY
G.hirsutum     MASTTMALSSPSFAGKAVKFSPSTPEIQGTGRVSMRKT-T--KPVP-SGSPWYGPDRVLY
S.tuberosum    MAAATMALSSPSFAGQAVKLSPSASEISGNGRITMRKAVA--KSAP-SSSPWYGPDRVKY
N.sylvestris   MAAATMALSSPSFAGQAVKLSPSASEITGNGRVSMRKTAA--KPVS-SSSPWYGPDRVKY
L.esculentum   MAAATMALSSPSFAGQAVKLSPSASEISGNGRITMRKAVA--KSAP-SSSPWYGPDRVKY
G.max          MAASTMALSSSSLAGQAIKLAPSTPEL-GVGRVSMRKTAS--KTVS-SGSPWYGPDRVKY
T.aestivum     MAATTMSLSSSSFAGKAVKNLPSS-ALIGDARVNMRKTAAKAKQVS-SSSPWYGSDRVLY
O.sativa       MAAATMALSSPALAGFAA---AKV---FGEGRITMRKSAARPKPAASSGSPWYGADRVLY
Z.mays         MASSTMALSSTAFAGKAVNVPSSS---FGEARVTMRKTAAKAKPAAASGSPWYGPDRVLY
               **  * ***    *     *  *   *  * ***  *       * ***** *** *

LS01           LGPLSG-EPPSYPTGEFPGDYGWDTAGLSADPETFAKNRELEVIHCRWAMLGALGCVFPE
L.gibba        LGPFSG-EAPSYLTGEFAGDYGWDTAGLSADPETFAKNRELEVIHARWAMLGALGCVFPE
G.hirsutum     LGPLSG-EPPSYLTGEFPGDYGWDTAGLSADPETFAKNRELEVIHCRWAMLGALGCVFPE
S.tuberosum    LGPFSG-ESPSYLTGEFPGDYGWDTAGLSADPETFAKNRELEVIHCRWAMLGALGCVFPE
N.sylvestris   LGPFSG-ESPSYLTSEFPGDYGWDTAGLSADPETFAKNRELEVIHCRWAMLGALGCVFPE
L.esculentum   LGPFSG-ESPSYLTGEFPGDYGWDTAGLSADPETFAKNRELEVIHCRWAMLGALGCVFPE
G.max          LGPFSG-EPPSYLTGEFPGDYGWDTAGLSADPETFAKNRELEVIHSRWAMLGALGCVFPE
T.aestivum     LGPLSG-EPPSYLTGEFPGDYGWDTAGLSADPETFAKNRELEVIHCRWAMLGALGCVFPE
O.sativa       LGPLSGREPPSYLTGEFPGDYGWDTAGLSADPETFAKNRELEVIHSRWAMLGGLGCVFPE
Z.mays         LGPLSG-EPPSYLTGEFPGDYGWDTAGLSADPETFAKNRELEVIHCRWAMLGALGCVFPE
               *** **  * ***  * ** ******************* ******* ****** *******

LS01           LLARNGVKFGEAVWFKAGAQIFSEGGLDYLGNPSLIHAQSILAIWACQVILMGAVEGYRV
L.gibba        LLARNGVKFGEAVWFKAGSQIFSEGGLDYLGNPSLVHAQSILAIWATQVVLMGAVEGYRV
G.hirsutum     LLARNGVKFGEAVWFKAGSQIFSEGGLDYLGNPSLIHAQSILAIWACQVVLMGAVEGYRI
S.tuberosum    LLARNGVKFGEAVWFKAGSQIFSEGGLDYLGNPSLVHAQSILAIWACQVVLMGAVEGYRI
N.sylvestris   LLARNGVKFGEAVWFKAGSQIFSEGGLDYLGNPSLVHAQSILAIWACQVILMGAVEGYRV
L.esculentum   LLARNGVKFGEAVWFKAGSQIFSEGGLDYLGNPSLVHAQSILAIWACQVVLMGAVEGYRI
G.max          LLSRNGVKFGEAVWFKAGSQIFSEGGLDYLGNPSLIHAQSILAIWATQVILMGAVEGYRI
T.aestivum     LLARNGVKFGEAGWFKAGSQIFSDGGLDYLGNPSLVHAQSLLAIWACQVVLMGAVEGYRI
O.sativa       LLARNGVKFGEAVWFKAGSQIFSEGGLDYLGNPSLIHAQSILAIWAVQVVLMGAVEGYRI
Z.mays         LLARNGVKFGEAVWFKAGSQIFSEGGLDYLGNPSLIHAQSILAIWACQVVLMGAVEGYRI
               ** ********* *****  **** ************ **** ****  ** *********

LS01           AGGPLGEVTDPLYPGGSFDPLGLADDPEAFAELKVKEIKNGRLAMFSMFGFFVQAIVTGK
L.gibba        AGGPLGEVVDPLYPGGSFDPLGLADDPEAFAELKVKEIKNGRLAMFSMFGFFVQAIVTGK
G.hirsutum     AGGPLGEVTDPLYPGGSFDPLGFADDPEAFAELKVKEIKNGRLAMFSMFGFFVQAIVTGK
S.tuberosum    AGGPLGEVVDPLYPGGSFDPLGLADDPEAFAELKVKEIKNGRLAMFSMFGFFVQAIVTGK
N.sylvestris   AGGPLGEVVDPLYPGGSFDPLGLAEDPEAFAELKVKEIKNGRLAMFSMFGFFVQAIVTGK
L.esculentum   AGGPLGEVVDPLYPGGSFDPLGLADDPEAFAELKVKEIKNGRLAMFSMFGFFVQAIVTGK
G.max          AGGPLGEVTDPIYPGGSFDPLGLADDPEAFAELKVKELKNGRLAMFSMFGFFVQAIVTGK
T.aestivum     AGGPLGEIVDPLYPGGSFDPLGLAERPQAFAELKVKEIKNGRLAMFSMFGFFVQAIVTGK
O.sativa       AGGPLGEVVDPLYPGGAFDPLGLADDPEAFAELKVKEIKNGRLAMFSMFGFFVQAIVTGK
Z.mays         AGGPLGEVVDPLYPGGSFDPLGLADDPEAFGELKVKELKKGRLAMLSMFGFFVQAIVTGK
               *******  ** **** ***** *    * ****** * **********************

LS01           GPLENLADHLADPVNNNAWAYATNFVPGK
L.gibba        GPLENLADHLADPVNNNAWAFATNFVPGK
G.hirsutum     GPLENLADHLADPVNNNAWAYATNFVPGK
S.tuberosum    GPLENLADHLADPVNNNAWAFATNFVPGK
N.sylvestris   GPLENLADHLADPVNNNAWAYATNFVPGK
L.esculentum   GPLENLADHLADPVNNNAWAFATNFVPGK
G.max          GPLENLADHLADPVNNNAWAYATNFVPGK
T.aestivum     GPLEDLADHLADPVNNNAWLIATNFVPGK
O.sativa       GPLENLADHLADPVNNNAWAYATNFVPGK
Z.mays         GPLENLADHIADPVNNNAWAYATNFVPGK
               ****  *** *********   ********
```

FIGURE 8

```
-932                                          AAAT AAAAAGATCG GATTCAAATT

-908 CAAAATTTTT TTATTCGATC CATATCTGGC TCGATCTATT TATATCCGAT TCAATCCGAT
         Motif AT-1

-848 TATCATCCCT AAAAAAAATC ATCATGCGTG CGGCCATTAT ATCATTAAAA TTGGTCATCT
                HSE

-788 TTATCCGGTG CTGCGCAAAT GGGTACATGT GGAGTGCCAT TGAATTGCTC CCGTGCAAGC

-728 GTGGCATGTC AACGTTCGAA TTAAGGGTAT GAGGAGCGTA TGGAATAGAT GGGGCGGGAG

-668 CCTAACAGGC TTATGTTGGC CTTGCTGGCT TGCTCGTGTT TGAACACGTT GGTGACCAAT
                ABA

-608 GAGCCATGGT TTGGTCATTT TTGGTCTAAG ATAATAAGTA TTTTTTTTTC TTTTTTCTCT

-548 TTTTGCTTTG ATAAATTAGA TTTATTAAAT CAATCTACAG TAAATGTATC CGTGAGCATC

-488 ACCGAAAATC CTCCTCTTAA AGAGGTCCGA CTAGACTGGG TTACATGCTA AGCAACTCAA

-428 AACTCAAATT CCAAATCAAG TCACTCATGC ACCGGCTCAA CTTGGTTTAG GGTAGACGAC
             WUN

-368 TGCCACTAGA ACGGTACATC TAGAACCTTC CGACCAGCTG TTTGATAAAA GTCAGGAGAT

-308 GTTTACATCA AAAATAAAGA TAAAAAATCG GGGATACGTG TAACTCCAAT TTACGCGTGG

-248 ATCCCAAGTC GTGGAGGGGC GACCACCGGG GAAGAAAATC TAGGAGGCCC AATCACAACT
                               G-box

-188 CAAGAACGAG ATTCCTAGCA GAAACCAATG CCCAAAGTAT CTGAAGCGCA GCTTGCCAGG

-128 TGTTCGACCA TTAGCCTTAA CCTCAAAGCC CATGAAGCAG CCAATCAAAT GAAAGAATTA
                                                 CCAAT box -68 GATTTCCTGG GATAAGGACT GCACCCGCCC CTCGTCTTTT AAGTCCCCTT AGACCCAACC
        GATA II   GATA I 51 CTTCACTCAG AGCACCTACC CAACAGCATT TCCATTGGGA TCACCGCTCC CATCTCCAAG
     Inr       ********* ****** ****** ****** ********

59 GCATCATC
   ** ** *** *
```

```
pGWLS1718    CTGTTTGATAAAAGTCAGGAGATGTTTACATCAAAAATAAAGATAAAAAATCGGGGATAC
LS01         ------------------------------------------------------------ pGWLS1718    GTGTAACTCCAATTTACGCGTGGATCCCAAGTCGTGGAGGGGCGACCACCGGGGAAGAAA
LS01         ------------------------------------------------------------ pGWLS1718    ATCTAGGAGGCCCAATCACAACTCAAGAACGAGATTCCTAGCAGAAACCAATGCCCAAAG
LS01         ------------------------------------------------------------ pGWLS1718    TATCTGAAGCGCAGCTTGCCAGGTGTTCGACCATTAGCCTTAACCTCAAAGCCCATGAAG
LS01         ------------------------------------------------------------ pGWLS1718    CAGCCAATCAAATGAAAGAATTAGATTTCCTGGGATAAGGACTGCACCCGCCCCTCGTCT
LS01         ------------------------------------------------------------ pGWLS1718    TTTAAGTCCCCTTAGACCCAACCCTTCACTCAGAGCACCTACCCAACAGCATTTCCATTG
LS01         ------------------------------AGAGCACCTACCCAACAGCATTTCCATTG
                                           **************************** pGWLS1718    GGATCACCGCTCCCATCTCCAAGGCATCATCTCTATCTAGTCCTTCTCA*ATG*GCTGCCAC
LS01         GGATCACCGCTCCCATCTCCAAGGCATCATCTCTATCTAGTCCTTCTCA*ATG*GCTGCCAC
             ************************************************************ pGWLS1718    CATGGCCCTCTCCTCCCCTTCCCTCGCCGGAAAAGCGGTGAAGCTCGCTCCCTCGGCCTC
LS01         CATGGCCCTCTCCTCCCCTTCCCTCGCCGGAAAAGCGGTGAAGCTCGCTCCCTCGGCCTC
             ************************************************************ pGWLS1718    TCCCATCCTCGGGAATGGCAGGGTCACCATGCGGAAGACCTCGACCAAGCGCGTCCCCTC
LS01         TCCCATCCTCGGGAATGGCAGGGTCACCATGCGGAAGACCTCGACCAAGCGCGTCCCCTC
             ************************************************************ pGWLS1718    CGGCAGCCCATGGTACGGGCCAGACCGTGTCAAGTACCTCGGCCCCTTGTCTGGGGAGCC
LS01         CGGCAGCCCATGGTACGGGCCAGACCGTGTCAAGTACCTCGGCCCCTTGTCTGGGGAGCC
             ************************************************************ pGWLS1718    CCCGTCCTACCTGACCGGTGAATTCCCCGGTGACTATGGGTGGGACACTGCTGGTCTCTC
LS01         CCCGTCCTACCTGACCGGTGAATTCCCCGGTGACTATGGGTGGGACACTGCTGGTCTCTC
             ************************************************************ pGWLS1718    GGCCGACCCTGAGACCTTCGCCAAGAACCGGGAGCTCGAGGTCATCCACTGCAGGTGGGC
LS01         GGCCGACCCTGAGACCTTCGCCAAGAACCGGGAGCTCGAGGTCATCCACTGCAGGTGGGC
             ************************************************************ pGWLS1718    CATGCTGGGTGCCCTCGGCTGCGTCTTTCCGGAGTTGCTTGCCCGCAATGGCGTCAAGTT
LS01         CATGCTGGGTGCCCTCGGCTGCGTCTTTCCGGAGTTGCTTGCCCGCAATGGCGTCAAGTT
             ************************************************************ pGWLS1718    CGGCGAGGCCGTCTGGTTCAAAGCGGGAGCTCAGATCTTCAGCGAGGGCGGTCTGGACTA
LS01         CGGCGAGGCCGTCTGGTTCAAAGCGGGAGCTCAGATCTTCAGCGAGGGCGGTCTGGACTA
             ************************************************************ pGWLS1718    CCTGGGCAACCCGAGCTTGATCCATGCTCAGAG---------------------------
LS01         CCTGGGCAACCCGAGCTTGATCCATGCTCAGAGCATTCTGGCCATCTGGGCTTGCCAAGT
             *********************************
```

Figure 14

```
pGWLS1718    ------------------------------------------------------------
LS01         TATACTGATGGGTGCCGTCGAAGGGTACCGCGTCGCCGGCGGTCCCCTGGGTGAGGTCAC pGWLS1718    ------------------------------------------------------------
LS01         CGACCCTCTGTACCCTGGGGGGAGCTTCGATCCCTTGGGCCTTGCCGATGACCCGGAGGC pGWLS1718    ------------------------------------------------------------
LS01         GTTCGCAGAGCTTAAAGTGAAAGAGATCAAGAACGGCAGGCTAGCCATGTTCTCCATGTT pGWLS1718    ------------------------------------------------------------
LS01         CGGTTTCTTTGTTCAGGCTATCGTGACCGGGAAGGGCCCGTTGGAGAACCTGGCCGACCA pGWLS1718    ------------------------------------------------------------
LS01         CCTTGCGGATCCTGTTAACAACAATGCTTGGGCCTACGCCACCAACTTCGTGCCCGGAAA pGWLS1718    ------------------------------------------------------------
LS01         GTGAGCCTGGCAACCTTAATTAATTTGGTGCTTAGAAATTCTTCATCTGTTGTGGTTTTT pGWLS1718    ------------------------------------------------------------
LS01         GTTTGAATTGAAATTGTTGGCGTGGTGTGCATTAAAAAAAAAAAAAAAAAAAAA
```

Figure 14 (cont.)

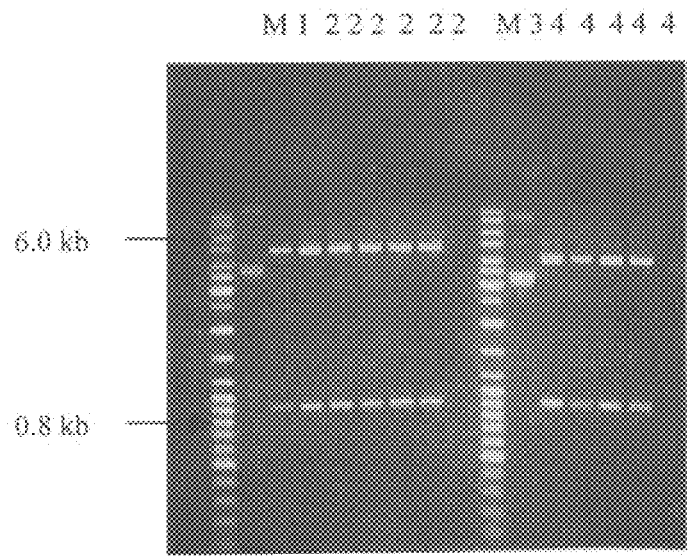

SEQUENCE LISTING

```
<160> NUMBER OF SEQ ID NOS: 39

<210> SEQ ID NO 1
<211> LENGTH: 992
<212> TYPE: DNA
<213> ORGANISM: Elaeis sp.

<400> SEQUENCE: 1
aaataaaaag atcggattca aattcaaaat tttttattc gatccatatc tggctcgatc      60
tatttatatc cgattcaatc cgattatcat ccctaaaaaa aatcatcatg cgtgcggcca    120
ttatatcatt aaaattggtc atctttatcc ggtgctgcgc aaatgggtac atgtggagtg    180
ccattgaatt gctcccgtgc aagcgtggca tgtcaacgtt cgaattaagg gtatgaggag    240
cgtatggaat agatggggcg ggagcctaac aggcttatgt tggccttgct ggcttgctcg    300
tgtttgaaca cgttggtgac caatgagcca tggtttggtc attttttggtc taagataata    360 agtatttttt tttcttttt ctcttttttgc tttgataaat tagatttatt aaatcaatct    420
acagtaaatg tatccgtgag catcaccgaa aatcctcctc ttaaagaggt ccgactagac    480
tgggttacat gctaagcaac tcaaaactca aattccaaat caagtcactc atgcaccggc    540
tcaacttggt ttagggtaga cgactgccac tagaacggta catctagaac cttccgacca    600
gctgtttgat aaaagtcagg agatgtttac atcaaaaata aagataaaaa atcggggata    660
cgtgtaactc caatttacgc gtggatccca agtcgtggag gggcgaccac cggggaagaa    720
```

```
aatctaggag gcccaatcac aactcaagaa cgagattcct agcagaaacc aatgcccaaa    780
gtatctgaag cgcagcttgc caggtgttcg accattagcc ttaacctcaa agcccatgaa    840
gcagccaatc aaatgaaaga attagatttc ctgggataag gactgcaccc gcccctcgtc    900
ttttaagtcc ccttagaccc aaccttcac tcagagcacc tacccaacag catttccatt    960
gggatcaccg ctcccatctc caaggcatca tc    992
```

<210> SEQ ID NO 2
<211> LENGTH: 264
<212> TYPE: PRT
<213> ORGANISM: Elaeis sp.

<400> SEQUENCE: 2

```
Met Ala Ala Thr Met Ala Leu Ser Ser Pro Ser Leu Ala Gly Lys Ala
1               5                   10                  15

Val Lys Leu Ala Pro Ser Ala Ser Pro Ile Leu Gly Asn Gly Arg Val
                20                  25                  30

Thr Met Arg Lys Thr Ser Thr Lys Arg Val Pro Ser Gly Ser Pro Trp
            35                  40                  45

Tyr Gly Pro Asp Arg Val Lys Tyr Leu Gly Pro Leu Ser Gly Glu Pro
        50                  55                  60

Pro Ser Tyr Leu Thr Gly Glu Phe Pro Gly Asp Tyr Gly Trp Asp Thr
65                  70                  75                  80

Ala Gly Leu Ser Ala Asp Pro Glu Thr Phe Ala Lys Asn Arg Glu Leu
                85                  90                  95

Glu Val Ile His Cys Arg Trp Ala Met Leu Gly Ala Leu Gly Cys Val
            100                 105                 110

Phe Pro Glu Leu Leu Ala Arg Asn Gly Val Lys Phe Gly Glu Ala Val
        115                 120                 125

Trp Phe Lys Ala Gly Ala Gln Ile Phe Ser Glu Gly Gly Leu Asp Tyr
130                 135                 140

Leu Gly Asn Pro Ser Leu Ile His Ala Gln Ser Ile Leu Ala Ile Trp
145                 150                 155                 160

Ala Cys Gln Val Ile Leu Met Gly Ala Val Glu Gly Tyr Arg Val Ala
                165                 170                 175

Gly Gly Pro Leu Gly Glu Val Thr Asp Pro Leu Tyr Pro Gly Gly Ser
            180                 185                 190

Phe Asp Pro Leu Gly Leu Ala Asp Asp Pro Glu Ala Phe Ala Glu Leu
        195                 200                 205

Lys Val Lys Glu Ile Lys Asn Gly Arg Leu Ala Met Phe Ser Met Phe
    210                 215                 220

Gly Phe Phe Val Gln Ala Ile Val Thr Gly Lys Gly Pro Leu Glu Asn
225                 230                 235                 240

Leu Ala Asp His Leu Ala Asp Pro Val Asn Asn Asn Ala Trp Ala Tyr
                245                 250                 255

Ala Thr Asn Phe Val Pro Gly Lys
            260
```

<210> SEQ ID NO 3
<211> LENGTH: 983
<212> TYPE: DNA
<213> ORGANISM: Elaeis sp.

<400> SEQUENCE: 3

```
agagcaccta cccaacagca tttccattgg gatcaccgct cccatctcca aggcatcatc    60
```

```
tctatctagt ccttctcaat ggctgccacc atggccctct cctcccttc cctcgccgga    120 aaagcggtga agctcgctcc ctcggcctct cccatcctcg ggaatggcag ggtcaccatg    180
cggaagacct cgaccaagcg cgtcccctcc ggcagcccat ggtacgggcc agaccgtgtc    240
aagtacctcg gcccttgtc tggggagccc ccgtcctacc tgaccggtga attccccggt    300
gactatgggt gggacactgc tggtctctcg gccgaccctg agaccttcgc caagaaccgg    360
gagctcgagg tcatccactg caggtgggcc atgctgggtg ccctcggctg cgtctttccg    420
gagttgcttg cccgcaatgg cgtcaagttc ggcgaggccg tctggttcaa agcgggagct    480
cagatcttca gcgagggcgg tctggactac ctgggcaacc cgagcttgat ccatgctcag    540
agcattctgg ccatctgggc ttgccaagtt atactgatgg gtgccgtcga agggtaccgc    600
gtcgccggcg gtcccctggg tgaggtcacc gaccctctgt accctggggg gagcttcgat    660
cccttgggcc ttgccgatga cccggaggcg ttcgcagagc ttaaagtgaa agagatcaag    720
aacggcaggc tagccatgtt ctccatgttc ggtttctttg ttcaggctat cgtgaccggg    780
aagggcccgt tggagaacct ggccgaccac cttgcggatc ctgttaacaa caatgcttgg    840
gcctacgcca ccaacttcgt gcccggaaag tgagcctggc aaccttaatt aatttggtgc    900
ttagaaattc ttcatctgtt gtggttttg tttgaattga aattgttggc gtggtgtgca    960
ttaaaaaaaa aaaaaaaaaa aaa                                          983
```

<210> SEQ ID NO 4
<211> LENGTH: 164
<212> TYPE: PRT
<213> ORGANISM: Elaeis sp.

<400> SEQUENCE: 4

```
Ala Asp Pro Glu Thr Phe Ala Lys Asn Arg Glu Leu Glu Val Ile His
1               5                   10                  15

Cys Arg Trp Ala Met Leu Gly Ala Leu Gly Cys Val Phe Pro Glu Leu
                20                  25                  30

Leu Ala Arg Asn Gly Val Lys Phe Gly Glu Ala Val Trp Phe Lys Ala
            35                  40                  45

Gly Ala Gln Ile Phe Ser Glu Gly Gly Leu Asp Tyr Leu Gly Asn Pro
        50                  55                  60

Ser Leu Ile His Ala Gln Ser Ile Leu Ala Ile Trp Ala Cys Gln Val
65                  70                  75                  80

Val Leu Met Gly Ala Val Glu Gly Tyr Arg Val Ala Gly Gly Pro Leu
                85                  90                  95

Gly Glu Val Thr Asp Pro Leu Tyr Pro Gly Gly Ser Phe Asp Pro Leu
                100                 105                 110

Gly Leu Ala Asp Asp Pro Glu Ala Phe Ala Glu Leu Lys Val Lys Glu
            115                 120                 125

Ile Lys Asn Gly Arg Leu Ala Met Phe Ser Met Phe Gly Phe Phe Val
        130                 135                 140

Gln Ala Ile Val Thr Gly Lys Gly Pro Leu Glu Asn Leu Ala Asp His
145                 150                 155                 160

Ile Ala Asp Pro
```

<210> SEQ ID NO 5
<211> LENGTH: 337
<212> TYPE: DNA
<213> ORGANISM: Elaeis

<400> SEQUENCE: 5

```
gcacgaggtt cgatcccttg ggccttgccg atgacccgga ggcgttcgca gagcttaaag      60
tgaaagagat caagaacggc aggctagcca tgttctccat gttcggtttc tttgttcagg     120
ctattgtgac cgggaagggc ccgttggaga acctggccga ccaccttgcg gatcctgtta     180
acaacaatgc ttgggcctac gccaccaact tcgtgcccgg aaagtgagcc tggcaacctt     240
aattaatttg gtgcttagaa attcttcatc tgttgtggtt tttgtttgaa ttgaaattgt     300
tggcgtggtg tgcattaaaa aaaaaaaaaa aaaaaa                               337
```

```
<210> SEQ ID NO 6
<211> LENGTH: 74
<212> TYPE: PRT
<213> ORGANISM: Elaeis sp.

<400> SEQUENCE: 6
```

```
Thr Arg Phe Asp Pro Leu Gly Leu Ala Asp Asp Pro Glu Ala Phe Ala
  1               5                  10                  15

Glu Leu Lys Val Lys Glu Ile Lys Asn Gly Arg Leu Ala Met Phe Ser
             20                  25                  30

Met Phe Gly Phe Phe Val Gln Ala Ile Val Thr Gly Lys Gly Pro Leu
         35                  40                  45

Glu Asn Leu Ala Asp His Leu Ala Asp Pro Val Asn Asn Asn Ala Trp
     50                  55                  60

Ala Tyr Ala Thr Asn Phe Val Pro Gly Lys
 65                  70
```

```
<210> SEQ ID NO 7
<211> LENGTH: 873
<212> TYPE: DNA
<213> ORGANISM: Elaeis sp.

<400> SEQUENCE: 7
ctgtttgata aaagtcagga gatgtttaca tcaaaaataa agataaaaaa tcggggatac      60
gtgtaactcc aatttacgcg tggatcccaa gtcgtggagg ggcgaccacc ggggaagaaa     120
atctaggagg cccaatcaca actcaagaac gagattccta gcagaaacca atgcccaaag     180
tatctgaagc gcagcttgcc aggtgttcga ccattagcct taacctcaaa gcccatgaag     240
cagccaatca aatgaaagaa ttagatttcc tgggataagg actgcacccg ccctcgtct     300 tttaagtccc cttagaccca acccttcact cagagcacct acccaacagc atttccattg     360
ggatcaccgc tcccatctcc aaggcatcat ctctatctag tccttctcaa tggctgccac     420
catggccctc tcctccccctt ccctcgccgg aaaagcggtg aagctcgctc cctcggcctc     480
tcccatcctc gggaatggca gggtcaccat gcggaagacc tcgaccaagc gcgtcccctc     540
cggcagccca tggtacgggc cagaccgtgt caagtacctc ggccccttgt ctggggagcc     600
cccgtcctac ctgaccggtg aattccccgg tgactatggg tgggacactg ctggtctctc     660
ggccgaccct gagaccttcg ccaagaaccg ggagctcgag gtcatccact gcaggtgggc     720
catgctgggt gccctcggct gcgtctttcc ggagttgctt gcccgcaatg gcgtcaagtt     780
cggcgaggcc gtctggttca aagcgggagc tcagatcttc agcgagggcg gtctggacta     840
cctgggcaac ccgagcttga tccatgctca gag                                  873
```

```
<210> SEQ ID NO 8
<211> LENGTH: 18
<212> TYPE: DNA
<213> ORGANISM: Artificial
<220> FEATURE:
<223> OTHER INFORMATION: Primer
```

```
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 8
gcngayccng aracntty                                                   18

<210> SEQ ID NO 9
<211> LENGTH: 18
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 9
cnggrtcngc datrtgrt                                                   18

<210> SEQ ID NO 10
<211> LENGTH: 961
<212> TYPE: DNA
<213> ORGANISM: Elaeis sp.

<400> SEQUENCE: 10
gcacctaccc aacagcattt ccattgggat caccgctccc atctccaagg catcatctct      60
atctagtcct tctcaatggc tgccaccatg gccctctcct cccccttccct cgccggaaaa    120 gcggtgaagc tcgctccctc ggcctctccc atcctcggga atggcagggt caccatgcgg    180
aagacctcga ccaagcgcgt cccctccggc agcccatggt acgggccaga ccgtgtcaag    240
tacctcggcc ccttgtctgg ggagccccg tcctacctga ccggtgaatt ccccggtgac     300
tatgggtggg acactgctgg tctctcggcc gaccctgaga ccttcgccaa gaaccgggag    360
ctcgaggtca tccactgcag gtgggccatg ctgggtgccc tcggctgcgt ctttccggag    420
ttgcttgccc gcaatggcgt caagttcggc gaggccgtct ggttcaaagc gggagctcag    480
atcttcagcg agggcggtct ggactacctg ggcaacccga gcttgatcca tgctcagagc    540
attctggcca tctgggcttg ccaagttata ctgatgggtg ccgtcgaagg gtaccgcgtc    600
gccggcggtc cctgggtga ggtcaccgac cctctgtacc ctgggggagg cttcgatccc    660
ttgggccttg ccgatgaccc ggaggcgttc gcagagctta aagtgaaaga gatcaagaac    720
ggcaggctag ccatgttctc catgttcggt ttctttgttc aggctatcgt gaccgggaag    780
ggcccgttgg agaacctggc cgaccacctt gcggatcctg ttaacaacaa tgcttgggcc    840
tacgccacca cttcgtgcc cggaaagtga gcctggcaac cttaattaat ttggtgctta    900
gaaattcttc atctgttgtg gtttttgttt gaattgaaat tgttggcgtg gtgtgcatta    960
a                                                                   961
```

```
<210> SEQ ID NO 11
<211> LENGTH: 91
<212> TYPE: DNA
<213> ORGANISM: Elaeis sp.

<400> SEQUENCE: 11
gcctggcaac cttaattaat ttggtgctta gaaattcttc atctgttgtg gtttttgttt    60
gaattgaaat tgttggcgtg gtgtgcatta a                                   91

<210> SEQ ID NO 12
<211> LENGTH: 30
<212> TYPE: DNA
<213> ORGANISM: Artificial
<220> FEATURE:
<223> OTHER INFORMATION: Primer

<400> SEQUENCE: 12
taatgcacac cacgccaaca atttcaattc                                     30

<210> SEQ ID NO 13
<211> LENGTH: 31
<212> TYPE: DNA
<213> ORGANISM: Artificial
<220> FEATURE:
<223> OTHER INFORMATION: Primer

<400> SEQUENCE: 13
gcctggcaac cttaattaat ttggtgctta g                                   31

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
gatgatgcct tggagatggg agcggtgatc                                     30

<210> SEQ ID NO 15
<211> LENGTH: 29
<212> TYPE: DNA
<213> ORGANISM: Artificial
<220> FEATURE:
<223> OTHER INFORMATION: Primer

<400> SEQUENCE: 15
gtgtcccacc catagtcacc ggggaattc                                      29

<210> SEQ ID NO 16
<211> LENGTH: 27
<212> TYPE: DNA
<213> ORGANISM: Artificial
<220> FEATURE:
<223> OTHER INFORMATION: Primer

<400> SEQUENCE: 16
gcacctaccc aacagcattt ccattgg                                        27

<210> SEQ ID NO 17
<211> LENGTH: 29
<212> TYPE: DNA
<213> ORGANISM: Artificial
<220> FEATURE:
<223> OTHER INFORMATION: Primer

<400> SEQUENCE: 17
```
cgaagttggt ggcgtaggcc caagcattg                                    29

<210> SEQ ID NO 18
<211> LENGTH: 29
<212> TYPE: DNA
<213> ORGANISM: Artificial
<220> FEATURE:
<223> OTHER INFORMATION: Primer

<400> SEQUENCE: 18
ctctgagcat ggatcaagct cgggttgcc                                    29

<210> SEQ ID NO 19
<211> LENGTH: 22
<212> TYPE: DNA
<213> ORGANISM: Artificial
<220> FEATURE:
<223> OTHER INFORMATION: Primer

<400> SEQUENCE: 19
gtaatacgac tcactatagg gc                                           22

<210> SEQ ID NO 20
<211> LENGTH: 19
<212> TYPE: DNA
<213> ORGANISM: Artificial
<220> FEATURE:
<223> OTHER INFORMATION: Primer

<400> SEQUENCE: 20
actatagggc acgcgtggt                                               19

<210> SEQ ID NO 21
<211> LENGTH: 23
<212> TYPE: DNA
<213> ORGANISM: Artificial
<220> FEATURE:
<223> OTHER INFORMATION: Primer

<400> SEQUENCE: 21
cccaagcttc catatctggc tcg                                          23

<210> SEQ ID NO 22
<211> LENGTH: 23
<212> TYPE: DNA
<213> ORGANISM: Artificial
<220> FEATURE:
<223> OTHER INFORMATION: Primer

<400> SEQUENCE: 22
tcccccgggc aatggaaatg ctg                                          23

<210> SEQ ID NO 23
<211> LENGTH: 22
<212> TYPE: DNA
<213> ORGANISM: Artificial
<220> FEATURE:
<223> OTHER INFORMATION: Primer

<400> SEQUENCE: 23
cgtcgccgtc cagctcgacc ag                                           22

<210> SEQ ID NO 24
<211> LENGTH: 16
<212> TYPE: DNA
<213> ORGANISM: Artificial

```
<220> FEATURE:
<223> OTHER INFORMATION: Primer

<400> SEQUENCE: 24
gtaaaacgac ggccag                                                    16

<210> SEQ ID NO 25
<211> LENGTH: 17
<212> TYPE: DNA
<213> ORGANISM: Artificial
<220> FEATURE:
<223> OTHER INFORMATION: Primer

<400> SEQUENCE: 25
caggaaacag ctatgac                                                   17

<210> SEQ ID NO 26
<211> LENGTH: 25
<212> TYPE: DNA
<213> ORGANISM: Artificial
<220> FEATURE:
<223> OTHER INFORMATION: Primer

<400> SEQUENCE: 26
cattgtttgc ctccctgctg cggtt                                          25

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
tgacgcatgt cgcgcaagac                                                20

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
atcctttcgc acgtaagtcc                                                20

<210> SEQ ID NO 29
<211> LENGTH: 266
<212> TYPE: PRT
<213> ORGANISM: Lemna gibba

<400> SEQUENCE: 29

Met Ala Ala Ser Met Ala Leu Ser Ser Pro Ser Leu Val Gly Lys Ala
1               5                   10                  15

Val Lys Leu Ala Pro Ala Ala Ser Glu Val Phe Gly Glu Gly Arg Val
                20                  25                  30

Ser Met Arg Lys Thr Ala Gly Lys Pro Lys Pro Val Ser Ser Gly Ser
            35                  40                  45

Pro Trp Tyr Gly Pro Asp Arg Val Lys Tyr Leu Gly Pro Phe Ser Gly
    50                  55                  60

Glu Ala Pro Ser Tyr Leu Thr Gly Glu Phe Ala Gly Asp Tyr Gly Trp
65                  70                  75                  80

Asp Thr Ala Gly Leu Ser Ala Asp Pro Glu Thr Phe Ala Lys Asn Arg
                85                  90                  95
```

Glu Leu Glu Val Ile His Ala Arg Trp Ala Met Leu Gly Ala Leu Gly
            100                 105                 110

Cys Val Phe Pro Glu Leu Leu Ala Arg Asn Gly Val Lys Phe Gly Glu
        115                 120                 125

Ala Val Trp Phe Lys Ala Gly Ser Gln Ile Phe Ser Glu Gly Gly Leu
    130                 135                 140

Asp Tyr Leu Gly Asn Pro Ser Leu Val His Ala Gln Ser Ile Leu Ala
145                 150                 155                 160

Ile Trp Ala Thr Gln Val Val Leu Met Gly Ala Val Glu Gly Tyr Arg
                165                 170                 175

Val Ala Gly Gly Pro Leu Gly Glu Val Val Asp Pro Leu Tyr Pro Gly
            180                 185                 190

Gly Ser Phe Asp Pro Leu Gly Leu Ala Asp Asp Pro Glu Ala Phe Ala
        195                 200                 205

Glu Leu Lys Val Lys Glu Ile Lys Asn Gly Arg Leu Ala Met Phe Ser
    210                 215                 220

Met Phe Gly Phe Phe Val Gln Ala Ile Val Thr Gly Lys Gly Pro Leu
225                 230                 235                 240

Glu Asn Leu Ala Asp His Leu Ala Asp Pro Val Asn Asn Asn Ala Trp
                245                 250                 255

Ala Phe Ala Thr Asn Phe Val Pro Gly Lys
            260                 265

<210> SEQ ID NO 30
<211> LENGTH: 264
<212> TYPE: PRT
<213> ORGANISM: Gossypium hirsutum

<400> SEQUENCE: 30

Met Ala Ser Thr Thr Met Ala Leu Ser Ser Pro Ser Phe Ala Gly Lys
1               5                   10                  15

Ala Val Lys Phe Ser Pro Ser Thr Pro Glu Ile Gln Gly Thr Gly Arg
            20                  25                  30

Val Ser Met Arg Lys Thr Thr Lys Pro Val Pro Ser Gly Ser Pro Trp
        35                  40                  45

Tyr Gly Pro Asp Arg Val Leu Tyr Leu Gly Pro Leu Ser Gly Glu Pro
    50                  55                  60

Pro Ser Tyr Leu Thr Gly Glu Phe Pro Gly Asp Tyr Gly Trp Asp Thr
65                  70                  75                  80

Ala Gly Leu Ser Ala Asp Pro Glu Thr Phe Ala Arg Asn Arg Glu Leu
                85                  90                  95

Glu Val Ile His Cys Arg Trp Ala Met Leu Gly Ala Leu Gly Cys Val
            100                 105                 110

Phe Pro Glu Leu Leu Ala Arg Asn Gly Val Lys Phe Gly Glu Ala Val
        115                 120                 125

Trp Phe Lys Ala Gly Ser Gln Ile Phe Ser Glu Gly Gly Leu Asp Tyr
    130                 135                 140

Leu Gly Asn Pro Ser Leu Ile His Ala Gln Ser Ile Leu Ala Ile Trp
145                 150                 155                 160

Ala Cys Gln Val Ile Leu Met Gly Ala Val Glu Gly Tyr Arg Ile Ala
                165                 170                 175

Gly Gly Pro Leu Gly Glu Val Thr Asp Pro Leu Tyr Pro Gly Gly Ser
            180                 185                 190

Phe Asp Pro Leu Gly Phe Ala Asp Asp Pro Glu Ala Phe Ala Glu Leu
        195                 200                 205

```
Lys Val Lys Glu Ile Lys Asn Gly Arg Leu Ala Met Phe Ser Met Phe
    210                 215                 220
Gly Phe Phe Val Gln Ala Ile Val Thr Gly Lys Gly Pro Leu Glu Asn
225                 230                 235                 240
Leu Ala Asp His Leu Ala Asp Pro Val Asn Asn Asn Ala Trp Ala Tyr
                245                 250                 255
Ala Thr Asn Phe Val Pro Gly Lys
            260
```

<210> SEQ ID NO 31
<211> LENGTH: 265
<212> TYPE: PRT
<213> ORGANISM: Solanum tuberosum

<400> SEQUENCE: 31

```
Met Ala Ala Ala Thr Met Ala Leu Ser Ser Pro Ser Phe Ala Gly Gln
1               5                   10                  15
Ala Val Lys Leu Ser Pro Ser Ala Ser Glu Ile Ser Gly Asn Gly Arg
                20                  25                  30
Ile Thr Met Arg Lys Ala Val Ala Lys Ser Ala Pro Ser Ser Ser Pro
            35                  40                  45
Trp Tyr Gly Pro Asp Arg Val Lys Tyr Leu Gly Pro Phe Ser Gly Glu
    50                  55                  60
Ser Pro Ser Tyr Leu Thr Gly Glu Phe Pro Gly Asp Tyr Gly Trp Asp
65                  70                  75                  80
Thr Ala Gly Leu Ser Ala Asp Pro Glu Thr Phe Ala Lys Asn Arg Glu
                85                  90                  95
Leu Glu Val Ile His Cys Arg Trp Ala Met Leu Gly Ala Leu Gly Cys
            100                 105                 110
Val Phe Pro Glu Leu Leu Ala Arg Asn Gly Val Lys Phe Gly Glu Ala
        115                 120                 125
Val Trp Phe Lys Ala Gly Ser Gln Ile Phe Ser Glu Gly Gly Leu Asp
    130                 135                 140
Tyr Leu Gly Asn Pro Ser Leu Val His Ala Gln Ser Ile Leu Ala Ile
145                 150                 155                 160
Trp Ala Cys Gln Val Val Leu Met Gly Ala Val Glu Gly Tyr Arg Ile
                165                 170                 175
Ala Gly Gly Pro Leu Gly Glu Val Val Asp Pro Leu Tyr Pro Gly Gly
            180                 185                 190
Ser Phe Asp Pro Leu Gly Leu Ala Asp Asp Pro Glu Ala Phe Ala Glu
        195                 200                 205
Leu Lys Val Lys Glu Ile Lys Asn Gly Arg Leu Ala Met Phe Ser Met
    210                 215                 220
Phe Gly Phe Phe Val Gln Ala Ile Val Thr Gly Lys Gly Pro Leu Glu
225                 230                 235                 240
Asn Leu Ala Asp His Leu Ala Asp Pro Val Asn Asn Asn Ala Trp Ala
                245                 250                 255
Phe Ala Thr Asn Phe Val Pro Gly Lys
            260                 265
```

<210> SEQ ID NO 32
<211> LENGTH: 265
<212> TYPE: PRT
<213> ORGANISM: Nicotiana sylvestris

<400> SEQUENCE: 32

```
Met Ala Ala Ala Thr Met Ala Leu Ser Ser Pro Ser Phe Ala Gly Gln
1               5                   10                  15

Ala Val Lys Leu Ser Pro Ser Ala Ser Glu Ile Thr Gly Asn Gly Arg
            20                  25                  30

Val Ser Met Arg Lys Thr Ala Ala Lys Pro Val Ser Ser Ser Ser Pro
        35                  40                  45

Trp Tyr Gly Pro Asp Arg Val Lys Tyr Leu Gly Pro Phe Ser Gly Glu
    50                  55                  60

Ser Pro Ser Tyr Leu Thr Ser Glu Phe Pro Gly Asp Tyr Gly Trp Asp
65                  70                  75                  80

Thr Ala Gly Leu Ser Ala Asp Pro Glu Thr Phe Ala Lys Asn Arg Glu
            85                  90                  95

Leu Glu Val Ile His Cys Arg Trp Ala Met Leu Gly Ala Leu Gly Cys
            100                 105                 110

Val Phe Pro Glu Leu Leu Ala Arg Asn Gly Val Lys Phe Gly Glu Ala
            115                 120                 125

Val Trp Phe Lys Ala Gly Ser Gln Ile Phe Ser Glu Gly Gly Leu Asp
            130                 135                 140

Tyr Leu Gly Asn Pro Ser Leu Val His Ala Gln Ser Ile Leu Ala Ile
145                 150                 155                 160

Trp Ala Cys Gln Val Ile Leu Met Gly Ala Val Glu Gly Tyr Arg Val
            165                 170                 175

Ala Gly Gly Pro Leu Gly Glu Val Val Asp Pro Leu Tyr Pro Gly Gly
            180                 185                 190

Ser Phe Asp Pro Leu Gly Leu Ala Glu Asp Pro Glu Ala Phe Ala Glu
            195                 200                 205

Leu Lys Val Lys Glu Ile Lys Asn Gly Arg Leu Ala Met Phe Ser Met
210                 215                 220

Phe Gly Phe Phe Val Gln Ala Ile Val Thr Gly Lys Gly Pro Leu Glu
225                 230                 235                 240

Asn Leu Ala Asp His Leu Ala Asp Pro Val Asn Asn Asn Ala Trp Ala
            245                 250                 255

Tyr Ala Thr Asn Phe Val Pro Gly Lys
            260                 265

<210> SEQ ID NO 33
<211> LENGTH: 265
<212> TYPE: PRT
<213> ORGANISM: Lycopersicon esculentum

<400> SEQUENCE: 33

Met Ala Ala Ala Thr Met Ala Leu Ser Ser Pro Ser Phe Ala Gly Gln
1               5                   10                  15

Ala Val Lys Leu Ser Pro Ser Ala Ser Glu Ile Ser Gly Asn Gly Arg
            20                  25                  30

Ile Thr Met Arg Lys Ala Val Ala Lys Ser Ala Pro Ser Ser Ser Pro
        35                  40                  45

Trp Tyr Gly Pro Asp Arg Val Lys Tyr Leu Gly Pro Phe Ser Gly Glu
    50                  55                  60

Ser Pro Ser Tyr Leu Thr Gly Glu Phe Pro Gly Asp Tyr Gly Trp Asp
65                  70                  75                  80

Thr Ala Gly Leu Ser Ala Asp Pro Glu Thr Phe Ala Lys Asn Arg Glu
            85                  90                  95

Leu Glu Val Ile His Cys Arg Trp Ala Met Leu Gly Ala Leu Gly Cys
            100                 105                 110
```

```
Val Phe Pro Glu Leu Leu Ala Arg Asn Gly Val Lys Phe Gly Glu Ala
        115                 120                 125

Val Trp Phe Lys Ala Gly Ser Gln Ile Phe Ser Glu Gly Gly Leu Asp
    130                 135                 140

Tyr Leu Gly Asn Pro Ser Leu Val His Ala Gln Ser Ile Leu Ala Ile
145                 150                 155                 160

Trp Ala Cys Gln Val Val Leu Met Gly Ala Val Glu Gly Tyr Arg Ile
                165                 170                 175

Ala Gly Gly Pro Leu Gly Glu Val Val Asp Pro Leu Tyr Pro Gly Gly
                180                 185                 190

Ser Phe Asp Pro Leu Gly Leu Ala Glu Asp Pro Glu Ala Phe Ala Glu
                195                 200                 205

Leu Lys Val Lys Glu Ile Lys Asn Gly Arg Leu Ala Met Phe Ser Met
    210                 215                 220

Phe Gly Phe Phe Val Gln Ala Ile Val Thr Gly Lys Gly Pro Leu Glu
225                 230                 235                 240

Asn Leu Ala Asp His Leu Ala Asp Pro Val Asn Asn Asn Ala Trp Ala
                245                 250                 255

Phe Ala Thr Asn Phe Val Pro Gly Lys
                260                 265

<210> SEQ ID NO 34
<211> LENGTH: 264
<212> TYPE: PRT
<213> ORGANISM: Glycine max

<400> SEQUENCE: 34

Met Ala Ala Ser Thr Met Ala Leu Ser Ser Ser Ser Leu Ala Gly Gln
1               5                   10                  15

Ala Ile Lys Leu Ala Pro Ser Thr Pro Glu Leu Gly Val Gly Arg Val
                20                  25                  30

Ser Met Arg Lys Thr Ala Ser Lys Thr Val Ser Ser Gly Ser Pro Trp
            35                  40                  45

Tyr Gly Pro Asp Arg Val Lys Tyr Leu Gly Pro Phe Ser Gly Glu Pro
50                  55                  60

Pro Ser Tyr Leu Thr Gly Glu Phe Pro Gly Asp Tyr Gly Trp Asp Thr
65                  70                  75                  80

Ala Gly Leu Ser Ala Asp Pro Glu Thr Phe Ala Lys Asn Arg Glu Leu
                85                  90                  95

Glu Val Ile His Ser Arg Trp Ala Met Leu Gly Ala Leu Gly Cys Val
                100                 105                 110

Phe Pro Glu Leu Leu Ser Arg Asn Gly Val Lys Phe Gly Glu Ala Val
        115                 120                 125

Trp Phe Lys Ala Gly Ser Gln Ile Phe Ser Glu Gly Gly Leu Asp Tyr
    130                 135                 140

Leu Gly Asn Pro Ser Leu Ile His Ala Gln Ser Ile Leu Ala Ile Trp
145                 150                 155                 160

Ala Thr Gln Val Ile Leu Met Gly Ala Val Glu Gly Tyr Arg Ile Ala
                165                 170                 175

Gly Gly Pro Leu Gly Glu Val Thr Asp Pro Ile Tyr Pro Gly Gly Ser
                180                 185                 190

Phe Asp Pro Leu Gly Leu Ala Asp Asp Pro Glu Ala Phe Ala Glu Leu
                195                 200                 205

Lys Val Lys Glu Leu Lys Asn Gly Arg Leu Ala Met Phe Ser Met Phe
    210                 215                 220
```

```
Gly Phe Phe Val Gln Ala Ile Val Thr Gly Lys Gly Pro Leu Glu Asn
225                 230                 235                 240

Leu Ala Asp His Leu Ala Asp Pro Val Asn Asn Asn Ala Trp Ala Tyr
            245                 250                 255

Ala Thr Asn Phe Val Pro Gly Lys
            260
```

<210> SEQ ID NO 35
<211> LENGTH: 266
<212> TYPE: PRT
<213> ORGANISM: Triticum aestivum

<400> SEQUENCE: 35

```
Met Ala Ala Thr Thr Met Ser Leu Ser Ser Ser Ser Phe Ala Gly Lys
1               5                   10                  15

Ala Val Lys Asn Leu Pro Ser Ser Ala Leu Ile Gly Asp Ala Arg Val
            20                  25                  30

Asn Met Arg Lys Thr Ala Ala Lys Ala Lys Gln Val Ser Ser Ser Ser
        35                  40                  45

Pro Trp Tyr Gly Ser Asp Arg Val Leu Tyr Leu Gly Pro Leu Ser Gly
50                  55                  60

Glu Pro Pro Ser Tyr Leu Thr Gly Glu Phe Pro Gly Asp Tyr Gly Trp
65                  70                  75                  80

Asp Thr Ala Gly Leu Ser Ala Asp Pro Glu Thr Phe Ala Lys Asn Arg
                85                  90                  95

Glu Leu Glu Val Ile His Cys Arg Trp Ala Met Leu Gly Ala Leu Gly
            100                 105                 110

Cys Val Phe Pro Glu Leu Leu Ala Arg Asn Gly Val Lys Phe Gly Glu
        115                 120                 125

Ala Gly Trp Phe Lys Ala Gly Ser Gln Ile Phe Ser Asp Gly Gly Leu
130                 135                 140

Asp Tyr Leu Gly Asn Pro Ser Leu Val His Ala Gln Ser Leu Leu Ala
145                 150                 155                 160

Ile Trp Ala Cys Gln Val Val Leu Met Gly Ala Val Glu Gly Tyr Arg
                165                 170                 175

Ile Ala Gly Gly Pro Leu Gly Glu Ile Val Asp Pro Leu Tyr Pro Gly
            180                 185                 190

Gly Ser Phe Asp Pro Leu Gly Leu Ala Glu Arg Pro Gln Ala Phe Ala
        195                 200                 205

Glu Leu Lys Val Lys Glu Ile Lys Asn Gly Arg Leu Ala Met Phe Ser
210                 215                 220

Met Phe Gly Phe Phe Val Gln Ala Ile Val Thr Gly Lys Gly Pro Leu
225                 230                 235                 240

Glu Asp Leu Ala Asp His Ile Ala Asp Pro Val Asn Asn Asn Ala Trp
                245                 250                 255

Leu Ile Ala Thr Asn Phe Val Pro Gly Lys
            260                 265
```

<210> SEQ ID NO 36
<211> LENGTH: 265
<212> TYPE: PRT
<213> ORGANISM: Oryza sativa

<400> SEQUENCE: 36

```
Met Ala Ala Ala Thr Met Ala Leu Ser Ser Pro Val Met Ala Arg Ala
1               5                   10                  15

Ala Pro Ser Thr Ser Ser Ala Leu Phe Gly Glu Ala Arg Ile Thr Met
```

```
                    20                  25                  30
Arg Lys Thr Ala Ala Lys Pro Lys Pro Ala Ala Ser Ser Gly Ser Pro
                35                  40                  45

Trp Tyr Gly Ala Asp Arg Val Leu Tyr Leu Gly Pro Leu Ser Gly Glu
            50                  55                  60

Pro Pro Ser Tyr Leu Thr Gly Glu Phe Pro Gly Asp Tyr Gly Trp Asp
65                  70                  75                  80

Thr Ala Gly Leu Ser Ala Asp Pro Glu Thr Phe Ala Lys Asn Arg Glu
                85                  90                  95

Leu Glu Val Ile His Ser Arg Trp Ala Met Leu Gly Ala Leu Gly Cys
            100                 105                 110

Val Phe Pro Glu Leu Leu Ala Arg Asn Gly Val Lys Phe Gly Glu Ala
        115                 120                 125

Val Trp Phe Lys Ala Gly Ser Gln Ile Phe Ser Glu Gly Gly Leu Asp
    130                 135                 140

Tyr Leu Gly Asn Pro Ser Leu Ile His Ala Gln Ser Ile Leu Ala Ile
145                 150                 155                 160

Trp Ala Val Gln Val Val Leu Met Gly Ala Val Glu Gly Tyr Arg Ile
                165                 170                 175

Ala Gly Gly Pro Leu Gly Glu Val Val Asp Pro Leu Tyr Pro Gly Gly
            180                 185                 190

Ala Phe Asp Pro Leu Gly Leu Ala Asp Asp Pro Glu Ala Phe Ala Glu
        195                 200                 205

Leu Lys Val Lys Glu Ile Lys Asn Gly Arg Leu Ala Met Phe Ser Met
    210                 215                 220

Phe Gly Phe Phe Val Gln Ala Ile Val Thr Gly Lys Gly Pro Leu Glu
225                 230                 235                 240

Asn Leu Ala Asp His Leu Ala Asp Pro Val Asn Asn Asn Ala Trp Ala
                245                 250                 255

Tyr Ala Thr Asn Phe Val Pro Gly Lys
            260                 265

<210> SEQ ID NO 37
<211> LENGTH: 265
<212> TYPE: PRT
<213> ORGANISM: Zea mays

<400> SEQUENCE: 37

Met Ala Ser Ser Thr Met Ala Leu Ser Ser Thr Ala Phe Ala Gly Lys
1               5                   10                  15

Ala Val Asn Val Pro Ser Ser Phe Gly Glu Ala Arg Val Thr Met
            20                  25                  30

Arg Lys Thr Ala Ala Lys Ala Lys Pro Ala Ala Ala Ser Gly Ser Pro
                35                  40                  45

Trp Tyr Gly Pro Asp Arg Val Leu Tyr Leu Gly Pro Leu Ser Gly Glu
            50                  55                  60

Pro Pro Ser Tyr Leu Thr Gly Glu Phe Pro Gly Asp Tyr Gly Trp Asp
65                  70                  75                  80

Thr Ala Gly Leu Ser Ala Asp Pro Glu Thr Phe Ala Lys Asn Arg Glu
                85                  90                  95

Leu Glu Val Ile His Cys Arg Trp Ala Met Leu Gly Ala Leu Gly Cys
            100                 105                 110

Val Phe Pro Glu Leu Leu Ala Arg Asn Gly Val Lys Phe Gly Glu Ala
        115                 120                 125

Val Trp Phe Lys Ala Gly Ser Gln Ile Phe Ser Glu Gly Gly Leu Asp
```

-continued

```
                130             135             140
Tyr Leu Gly Asn Pro Ser Leu Ile His Ala Gln Ser Ile Leu Ala Ile
145                 150                 155                 160

Trp Ala Cys Gln Val Val Leu Met Gly Ala Val Glu Gly Tyr Arg Ile
                165                 170                 175

Ala Gly Gly Pro Leu Gly Glu Val Val Asp Pro Leu Tyr Pro Gly Gly
                180                 185                 190

Ser Phe Asp Pro Leu Gly Leu Ala Asp Pro Glu Ala Phe Gly Glu
                195                 200                 205

Leu Lys Val Lys Glu Leu Lys Lys Gly Arg Leu Ala Met Leu Ser Met
                210                 215                 220

Phe Gly Phe Phe Val Gln Ala Ile Val Thr Gly Lys Gly Pro Leu Glu
225                 230                 235                 240

Asn Leu Ala Asp His Ile Ala Asp Pro Val Asn Asn Ala Trp Ala
                    245                 250                 255

Tyr Ala Thr Asn Phe Val Pro Gly Lys
                260                 265

<210> SEQ ID NO 38
<211> LENGTH: 11
<212> TYPE: DNA
<213> ORGANISM: Lemna gibba

<400> SEQUENCE: 38
caaattccaa a                                                       11

<210> SEQ ID NO 39
<211> LENGTH: 493
<212> TYPE: DNA
<213> ORGANISM: Elaeis sp.

<400> SEQUENCE: 39
gctgatccgg agaccttcgc caagaaccgt gagctcgagg tcatccactg ccgttgggcc    60
atgctcggcg ctcttggctg cgtcttcccg gagcttctcg cacgcaacgg cgtcaagttc   120
ggcgaggccg tctggttcaa ggctggtgcc cagatcttta gtgagggtgg tctggactac   180
ttgggcaacc ccagcctgat ccacgctcag agcattctgg ccatctgggc ctgccaagtt   240
gtattgatgg gcgccgtcga gggtaccgc gtcgccggtg ggccgctagg tgaggtcacc    300
gacccgctgt atcccggtgg gagcttcgat cccttggggt tggccgatga cccggaggct   360
ttcgcagaac ttaaagtgaa ggagatcaag aacggcagac tggccatgtt ctccatgttc   420
gggttctttg ttcaggctat cgtcactggc aagggtccgt tggagaactt ggccgaccac   480
atcgcggacc cag                                                    493
```

LEAF-SPECIFIC CHLOROPHYLL A/B BINDING PROTEIN GENE PROMOTER FROM OIL PALM

RELATED APPLICATION

This application is a continuation of U.S. patent application Ser. No. 11/452,065, filed Jun. 13, 2006 and now issued as U.S. Pat. No. 7,629,454, which is incorporated by reference herein in its entirety.

TECHNICAL FIELD OF THE INVENTION

The invention is related to type I chlorophyll a/b binding protein gene with abundant and specific expression in the leaf of the Palmae family, its regulatory sequence, and the use of its regulatory sequence for controlling the expression of foreign genes to produce high value-added products in the leaves of transgenic plants.

SUMMARY OF THE INVENTION

The present invention relates to the promoter sequence of the light-harvesting chlorophyll a/b binding protein gene pGWLS01 which was isolated from the oil palm genome. The presence of this promoter sequence will enable the manipulation of oil palm leaves for producing high value-added product via the introduction of foreign genes into the oil palm genome using genetic engineering tools. Furthermore, the promoter is also potentially useful in the production of insect resistant palm for the purpose of crop protection. The novel features of the promoter itself which regulate high and specific expression of foreign genes in the leaves will avoid the interference of novel products in the commodity oil extracted from mesocarp and kernel tissues. The presence of leaves throughout the plant life cycle will also enable early harvesting and continuous supply of novel metabolites.

Three different approaches (RT-PCR, cDNA library screening and 5'-RACE) were employed in the isolation of cDNA that encodes for the light-harvesting chlorophyll a/b binding protein gene (LS01). RT-PCR and screening of leaf cDNA library resulted in the isolation of partial LS01 cDNA sequence with poly(A)$^+$ tail. Subsequently 5'-RACE reaction produced a full-length sequence of LS01. This clone was found to exhibit 86% and above homology at the amino acid level with the deduced amino acid sequences of Lhcb 1 of photosystem 11 cDNAs isolated from 9 different monocot and dicot plants (GenBank database). Furthermore, the ORF of LS01 gene also encodes for both transit peptide and mature protein. The transit peptide is required for the transportation of LS01 gene into the chloroplast.

The gene copy number of LS01 was determined by Southern blot analysis. The 3' end gene-specific probe used in the analysis was able to distinguish LS01 from other members of this gene family. Only one copy of this gene is found in the oil palm genome. In the Northern analysis, expression of LS01 transcript was high and strong in the young and mature green leaves. As for yellowish spear leaves, lower level of expression was observed. However, the expression of LS01 transcript was not detected in the non-photosynthetic tissues such as kernel, mesocarp, germinated seedlings and flower.

The genome walking approach was successfully used for isolating the LS01 promoter. The presence of gene-specific primers in both primary and secondary PCR was able to amplify the genomic clone of interest from a pool of digested and adaptor ligated genomic DNA. In addition, the same approach was also utilized to study the structure of LS01 genomic clone. It was observed that introns were absent from the LS01 genomic sequence.

The strength and specificity of LS01 promoter was confirmed by a transient assay system and transgenic analysis using model plant, *Arabidopsis thaliana*. In the transient GUS assay, LS01 promoter was cloned into pBI221 vector carrying GUS as a reporter gene after removal of 35S CaMV promoter. As for transient GFP assay, LS01 promoter was cloned into pEGFP promoterless vector carrying GFP as a reporter gene. Both of the plasmids DNA were used in the bombardment of oil palm leaf tissues and mesocarp slices as control. Results obtained from the GUS assay and GFP detection confirmed that LS01 promoter was able to drive the expression of the reporter genes only in the leaf tissue. In the *Arabidopsis* work, the model plant was transformed with *Agrobacterium* carrying a binary vector harboring the leaf-specific promoter controlling a reporter gene (GUS). Transgenic plant carrying the leaf specific promoter was planted until the third generation in order to obtain a stable integration of the transgenes in the *Arabidopsis* genome. Results from the GUS staining of the *Arabidopsis* seedling further confirmed the leaf specificity of LS01 promoter.

Accordingly, it is the primary object of the present invention to provide a promoter sequence of chlorophyll a/b binding protein gene isolated from oil palm, wherein the promoter sequence exhibits leaf-specificity.

It is another object of the present invention to provide a promoter sequence for controlling leaf-specific expression of foreign genes encoding protein.

It is another object of the present invention to use the complete or partial sequence of LS01 cDNA or promoter for isolation of promoter or regulatory sequence.

It is yet another object of the present invention to provide a recombinant DNA construct containing LS01 promoter for transforming plant cells, plant tissues or parts of plants.

It is yet another object of the present invention to provide transgenic plants resulting from recombinant DNA constructs, to produce high value-added products, monoclonal antibodies, vaccine and other useful industrial or pharmaceutical products.

These and other objects of the present invention are accomplished by providing,

An isolated nucleic acid comprising a regulatory nucleic acid sequence that is at least 50% identical to the sequence set forth in SEQ ID NO: 1 or a complement thereof after optimal alignment.

and

An isolated nucleic acid encoding an amino acid sequence set forth in SEQ ID NO: 2 or an amino acid sequence that has greater than 70% similarity to SEQ ID NO: 2 after optimal alignment.

and

A nucleic acid construct, comprising a nucleic acid as claimed in the present invention, wherein the nucleic acid is operably linked to a recombined nucleic acid.

and

A vector comprising the nucleic acid construct as claimed in the present invention.

and

The nucleic acid construct as claimed in this invention, wherein the recombined (nucleic acid) encodes a protein that impart insect resistance, production of bioplastic, production of nutraceutical products, production of pharmaceutical macromolecules including therapeutic and diagnostic protein, antibodies and vaccines or result in an increase in photosynthetic rate of plant, or result in changes of plant shade.

and

A cell comprising the nucleic acid construct as claimed in the present invention.

and

A transgenic plant comprising the nucleic acid construct as claimed in the present invention.

BRIEF DESCRIPTION OF THE FIGURES

FIG. 1 shows the products of RT-PCR using primer CAB (F) and CAB(R). Lane M is the DNA Ladder Mix Marker. Lane 1 and 2 are the 500 by products amplified from the pool of expressed gene in oil palm leaves.

FIG. 2 provides the nucleotide (SEQ ID NO: 39) and deduced amino acid (SEQ ID NO:4) sequences of pRTLS01. The amino acids are shown in single letter codes. The sequence is part of Lhcb gene coding region.

FIG. 7 provides the nucleotide (SEQ ID NO:3) and deduced amino acid (SEQ ID NO:2) sequences of LS01 complete cDNA sequence. The derived amino acids are presented in single letter codes. The putative transcription start site is bold and italic. The translation start site is indicated in boldface. The transit peptide is underlined. The position marked by brackets denotes the first predicted amino acid of the mature protein. The consensus sequences for polyadenylation signals are underlined and italic. The stop codon (TGA) is denoted by asterisk (*).

FIG. 8 provides the comparison of the deduced amino acid sequence of LS01 (SEQ ID NO:2) with Lhcb I amino acid sequences from other plants. The conserved first predicted amino acid of the mature protein was underlined. Dots have been introduced to optimize alignment. Asterisk (*) represent identical amino acids. The GenBank accession number of the sequences are as follows: duckweed (*L. gibba* AAA33396; SEQ ID NO:29), cotton (*G. hirsutum* AAA18529, SEQ ID NO:30), potato (*S. tuberosum* AAA80589, SEQ ID NO:31), tobacco (*N. sylvestris* BAA25388, SEQ ID NO:32), tomato (*L. esculentum* AAA34137, P07370, SEQ ID NO:33), soya bean (*G. max* AAA50172, SEQ ID NO:34), wheat (*T. aestivum* P04784, SEQ ID NO:35), rice (*O. sativa* P12330, SEQ ID NO:36) and maize (*Z. mays* P06671, SEQ ID NO:37).

FIG. 12 provides the nucleotide sequence of the oil palm LS01 promoter, pGWLS01 (SEQ ID NO:1). Putative transcription start site is shown in italics. Asterisk (*) represent the overlapping sequences with 5'-UTR of LS01 gene. Several putative cis-acting elements were identified and underlined. These consist of initiator element (Inr), I-box, GATA box, CCAAT box, G-box, wound responsive element (WUN), abscisic acid responsive element (ABA) and heat-shock responsive element (HSE).

FIG. 14 provides the alignment result of genomic clone, pGWLS1718 (SEQ ID NO:7) and cDNA clone, LS01 (SEQ ID NO:3). Asterisk (*) represent the conserved nucleotides in both sequences. The translation start site (ATG) is bold and italic. Transcription start site is bold and underlined.

FIG. 15 shows the results for restriction enzymes analysis of plasmid pLS01GUS and pLS01GFP using Sma I and Hind 111. Lane M is the DNA Ladder Mix Marker. Lanes 1 and 3 are the undigested plasmid of pLS01GUS and pLS01GFP, respectively. Lanes 2 and 4 are the digested plasmid of pLS01GUS and pLS01GFP, respectively.

BRIEF DESCRIPTION OF THE TABLES

Figures 3, 4:
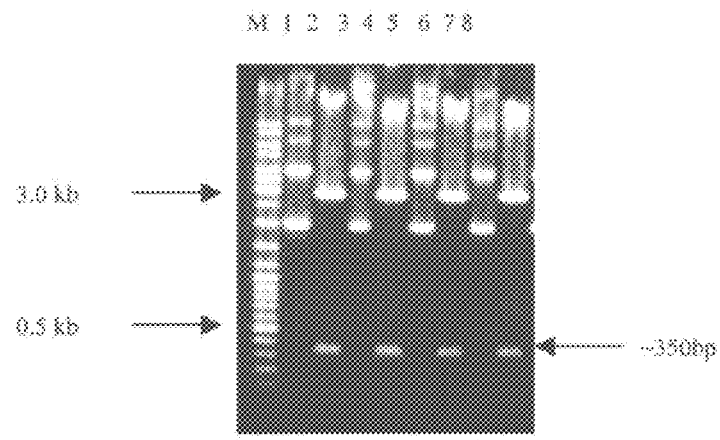
FIG. 3 shows the results of digested phagemids on 1.0% agarose gel. The phagemids were obtained from in vivo excision of putative clones from secondary library screening. Lane M is the DNA Ladder Mix Marker. Lanes 1, 3, 5 and 7 are the undigested phagemids. Lanes 2, 4, 6 and 8 are the phagemids digested with EcoR I and Xho 1.
FIG. 4 provides the nucleotide (SEQ ID NO:5) and deduced amino acid (SEQ ID NO:6) sequences of pLS01 which was obtained from the screening of oil palm leaf cDNA library. The derived amino acids are presented in single letter codes. The consensus sequences for polyadenylation signal are underlined. The stop codon (TGA) is denoted by asterisk (*).

Table 1 summarizes the score value and percentage of identity obtained from BLASTX analysis of LS01 sequence using GenBank database.

| Brief Description of the Sequences | | |
|---|---|---|
| Sequence ID No. | Sequence identity | Description of sequence |
| 1 | pGWLS01 | Oil palm chlorophyll a/b binding protein (LS01) promoter sequence |
| 2 | LS01 | Oil palm chlorophyll a/b binding protein amino acid sequence |
| 3 | LS01 | Oil palm chlorophyll a/b binding protein gene complete ORF sequence |
| 4 | pRTLS01 | Partial LS01 isolated from RT-PCR, amino acid sequence |
| 5 | pLS01 | Partial LS01 isolated from cDNA library, nucleotide sequence |
| 6 | pLS01 | Partial LS01 isolated from cDNA library, amino acid sequence |
| 7 | pGWLS1718 | Genomic sequence obtained from PCR using primers LS17 and LS18 |
| 8 | CAB(F) | Forward degenerate primer for amplification of partial LS01 using RT-PCR |
| 9 | CAB(R) | Reverse degenerate primer for amplification of partial LS01 using RT-PCR |
| 10 | LS1 | Entire sequence of LS01 cDNA fragment amplified for Northern blot analysis |
| 11 | LS2 | 3'-UTR of LS01 cDNA fragment amplified for Northern blot analysis |
| 12 | LS10 | Antisense primer for amplification of LS1 and LS2 |
| 13 | LS11 | Sense primer for amplification of LS2 |
| 14 | LS12 | Nested gene-specific primer for amplification of pGWLS01 |
| 15 | LS14 | Gene-specific primer for amplification of pGWLS01 |
| 16 | LS15 | Sense primer for amplification of LS1 |
| 17 | LS17 | Gene-specific primer for amplification of pGWLS1718 |

-continued

Brief Description of the Sequences

| Sequence ID No. | Sequence identity | Description of sequence |
|---|---|---|
| 18 | LS18 | Nested gene-specific primer for amplification of pGWLS1718 |
| 19 | AP1 | Adaptor-specific primer for amplification of pGWLS01 and pGWLS1718 |
| 20 | AP2 | Nested adaptor-specific primer for amplification of pGWLS01 and pGWLS1718 |
| 21 | LS221c | Sense primer for amplification of leaf-specific promoter fragment from plasmid pGWLS01 |
| 22 | LS221d | Antisense primer for amplification of leaf-specific promoter fragment from plasmid pGWLS01 |
| 23 | EGFPN | Primer for sequencing of plasmid pLS01GFP |
| 24 | M13F | Forward primer for sequencing of plasmid pLS01GUS |
| 25 | M13R | Reverse primer for sequencing of plasmid pLS01GUS |
| 26 | GUS-lower | Primer for detection of gus gene in DNA construct pBI101LS01 |
| 27 | GUSFOR | Forward primer for detection of gus gene in genomic DNA of transgenic plant |
| 28 | GUSREV | Reverse primer for detection of gus gene in genomic DNA of transgenic plant |
| 29 | *Solanum tuberosum* | *Solanum tuberosum* Lhcb I amino acid sequence |
| 30 | *Nicotiana sylvestris* | *Nicotiana sylvestris* Lhcb I amino acid sequence |
| 31 | *Lycopersicon esculentum* | *Lycopersicon esculentum* Lhcb I amino acid sequence |
| 32 | *Gossypium hirsutum* | *Gossypium hirsutum* Lhcb I amino acid sequence |
| 33 | *Glycine max* | *Glycine max* Lhcb I amino acid sequence |
| 34 | *Lemna gibba* | *Lemna gibba* Lhcb I amino acid sequence |
| 35 | *Zea mays* | *Zea mays* Lhcb I amino acid sequence |
| 36 | *Oryza saliva* | *Oryza saliva* Lhcb I amino acid sequence |
| 37 | *Triticum aestivum* | *Triticum aestivum* Lhcb I amino acid sequence |
| 38 | WUN | Wound-responsive element |
| 39 | pRTLS01 | Partial LS01 isolated from RT-PCR, nucleotide sequence |

DETAILED DESCRIPTION OF THE INVENTION

Sense degenerate primer, CAB(F) and antisense degenerate primer, CAB(R) which were derived from the conserved region of light harvesting chlorophyll a/b binding protein (Lhcb) gene from three different monocotyledonous plants consist of maize, rice and grain were used to amplify the related gene from oil palm cDNA pool. Incorporation of these primers in the PCR reaction resulted in the isolation of 500 by Lhcb gene from the single stranded leaf cDNA pool derived from reverse transcription of leaf mRNA (FIG. 1). The nucleotide and deduced amino acid sequence of this clone was designated pRTLS01 (FIG. 2). BLASTX analysis using GenBank non-redundant database showed that pRTLS01 has 85% and 84% homology with deduced amino acid sequences from maize and rice, respectively. These homologies were expected as the degenerate primers were designed based on the maize and rice sequences. Sequence of pRTLS01 was found to code for open reading frame (ORF) of Lhcb gene.

Figures 5, 6:
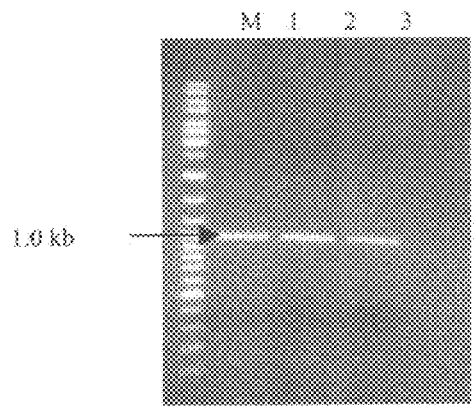
FIG. 5 shows the alignment between deduced amino acid sequences of pRTLS01 (SEQ ID NO:4) and pLS01 (SEQ ID NO:6). Identical amino acids in both sequences are presented by asterisk (*). A total of 96% homology was observed.
FIG. 6 shows the products of SMART RACE that was amplified from the 5'-RACE-Ready cDNA using gene-specific primer, LS 10. Lane M is the DNA Ladder Mix Marker. Lanes 1, 2 and 3 are the 1.0 kb products of SMART RACE.

Primary screening of leaf cDNA library using radioactive labeled pRTLS01 resulted in the detection of 61 putative oil palm Lhcb clones. After secondary screening, the number of putative clone was reduced to 30. In vivo excision and restriction enzyme analysis of the isolated recombinant phagemids prior to sequencing confirmed that all the clones have the same insert size of 350 by (FIG. 3). Based on the nucleotide and deduced amino acid sequences, this clone designated pLS01 consists of 224 by ORF, 89 by 3'-untranslated region (3'-UTR) and poly(A)$^+$ tail (FIG. 4). A stop codon (TGA) was observed at position 225 bp. Furthermore, two imperfect consensus signals for polyadenylation, AATAAA and TGT-GTTTT were also found at 14 by and 48 bp, respectively downstream from the TGA stop codon. Both of the imperfect sequences motif were also observed in the 3'-UTR of Scots pine Lhcb cDNA (Jansson & Gustafsson 1990). The ORF of pLS01 also showed a very high homology, 96% with part of the ORF from pRTLS01 (FIG. 5).

5'-RACE approach was carried out to obtain the full-length cDNA sequence and to determine the transcription start site of oil palm Lhcb gene. Based on the sequence information of pLS01, an antisense gene-specific primer, LS10 located prior to the poly(A)$^+$ tail of this clone was designed. The presence of primer LS10 and adaptor primer from the kit in the PCR reaction of 5'-RACE-Ready cDNA had resulted in the amplification of 1.0 kb distinct band (FIG. 6). The nucleotide and deduced amino acid sequences of this clone were designated LS01 (FIG. 7). Analysis on both of the sequences revealed that LS01 represent the full-length clone of Lhcb gene in oil palm. The adenine at the 5' end of the LS01 sequence is predicted to be the putative transcription start site of this gene. This clone contains a 5'-untranslated region of 78 bp, an ORF of 795 by and a 3'-untranslated region of 89 bp. The ORF of this clone was found to encode for 265 amino acid protein. A total of 33 amino acids make up the transit peptide and another 232 make up the mature protein. As Lhcb gene is a nuclear encoded gene, transit peptide is required for the transportation of this gene into the chloroplast (Mullet 1993). Transit peptide was also found in the Lhcb gene isolated from other plant species such as maize, tobacco, rice and tomato (Demmin et al. 1989).

Table 1 shows the results obtained from BLASTX identity search for LS01 clone using GenBank database. This clone exhibited 86% and above homology with the deduced amino acid sequence of photo system 11 isolated from 9 different monocot and dicot plants. Alignment of LS01 deduced amino acid sequence with the sequences from other plant species in FIG. 8 showed that the region coding for mature protein in highly conserved as compared to the region of transit peptide. Furthermore, a conserved amino acid motif for the start of mature protein, MRK was also observed in all the plants.

TABLE 1

| Organisms | GenBank Identification No. | Score Value | Percentage of Identity (%) |
|---|---|---|---|
| Solanum tuberosum | AAA80589 | 509 | 92 |
| Nicotiana sylvestris | BAA25388 | 508 | 93 |
| Lycopersicon esculentum | AAA34147 | 508 | 92 |
| Gossypium hirsutum | AAA18529 | 506 | 93 |
| Glycine max | AAA50172 | 499 | 92 |
| Lemna gibba | AAA33396 | 496 | 90 |
| Zea mays | P06671 | 481 | 88 |
| Oryza sativa | P12331 | 475 | 89 |
| Triticum aestivum | P04784 | 469 | 86 |

In the Lhcb multigene family of photosystem II, different types of Lhcb (Lhcb1, Lhcb2 and Lhcb3) can be identified based on the amino acid characteristic of transit peptide and mature protein of cDNA clone or the presence of intron in the genomic clone (Demmin et al. 1989; Chinn et al. 1995). The oil palm full-length LS01 has the comparable structure and number of amino acid as observed in the Lhcb1 of *Glycine max* (Stockinger & Walling 1994), *Gossypium hirsutum* (Anderson et al. 1993) and *Solanum tuberosum* (Fernandez et al. 1995). According to Buetow et al. (1988), Lhcb1ORF normally comprises of 31 to 37 amino acids for transit peptide and 231 to 235 amino acids for mature protein. Based on the results of BLASTX identity search and characteristic of amino acid, it is confirmed that oil palm LS01 belongs to the Lhcb1 gene family.

Figure 9:
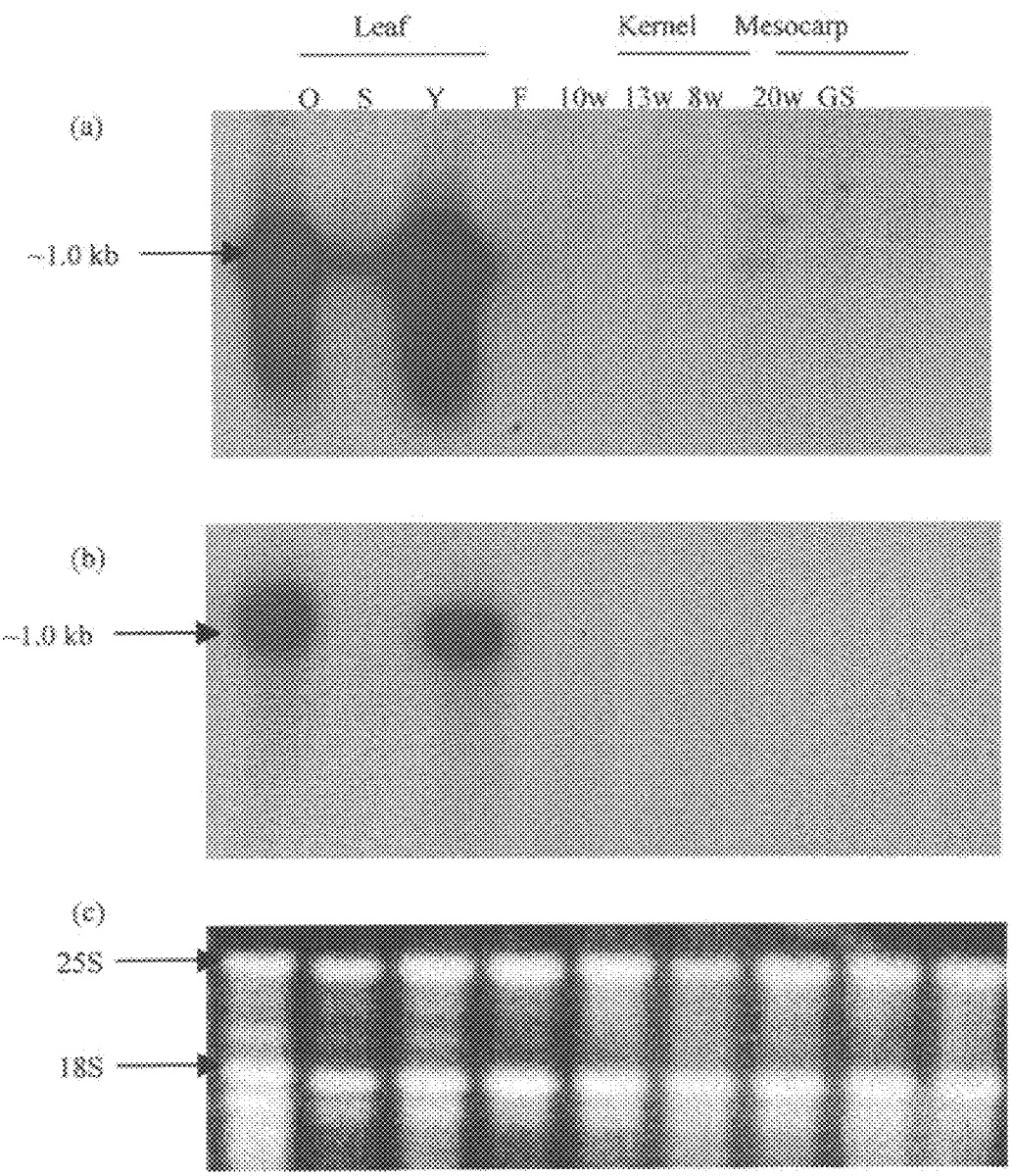
FIG. 9 provides the results of Northern blot analysis using two different PCR produced probes, LS1 and LS2 containing the entire sequence of LS01 (9a) and 3'-UTR of LS01 (9b), respectively. Total RNA (5 μg/lane) was size fractionated on 1.2% agarose gel and transferred to nylon membrane prior to hybridization with $^{32}$P-labeled LS1 and LS2 probes. M, S, Y, F and GS represent total RNA isolated from mature leaves, spear leaves, young leaves, flower and germinated seedlings. The alphabet 'w' represents week after anthesis. An ethidium bromide stained gel (9c) was included to show the equal loading of total RNA from various oil palm tissues.

Northern blot analysis was carried out to determine the expression patterns of the oil palm Lhcb gene in various oil palm tissues. Two PCR produced probes LS1 and LS2 containing entire sequence of LS01 and 3'-UTR of LS01, respectively were hybridized with the Northern blots. It was observed that both of the probes hybridized to a single transcript of approximately 1.0 kb (FIGS. 9a and 9b). Furthermore, the expression of LS01 gene was very strong, specific and developmentally regulated in the leaf tissues. High expression of LS01 was detected in the young and mature green leaves. As for yellowish spear leaves, lower level of expression was observed. The expression of LS01 was not detected in the non-photo synthetic tissues such as kernel, mesocarp, germinated seedlings and flower.

Intensity of the signal observed in the nylon membrane hybridized with probe LS1 is higher than with probe LS2. The differences indicated that the entire sequence of LS01 hybridized with the entire mRNA transcript that contained the conserved coding region of Lhcb gene. Whereas the 3'-UTR probe enable the specific analysis of individual gene because only LS01 transcript was hybridized. These results revealed that beside LS01, other members of the Lhcb gene could be present in the oil palm leaves.

Figure 10:
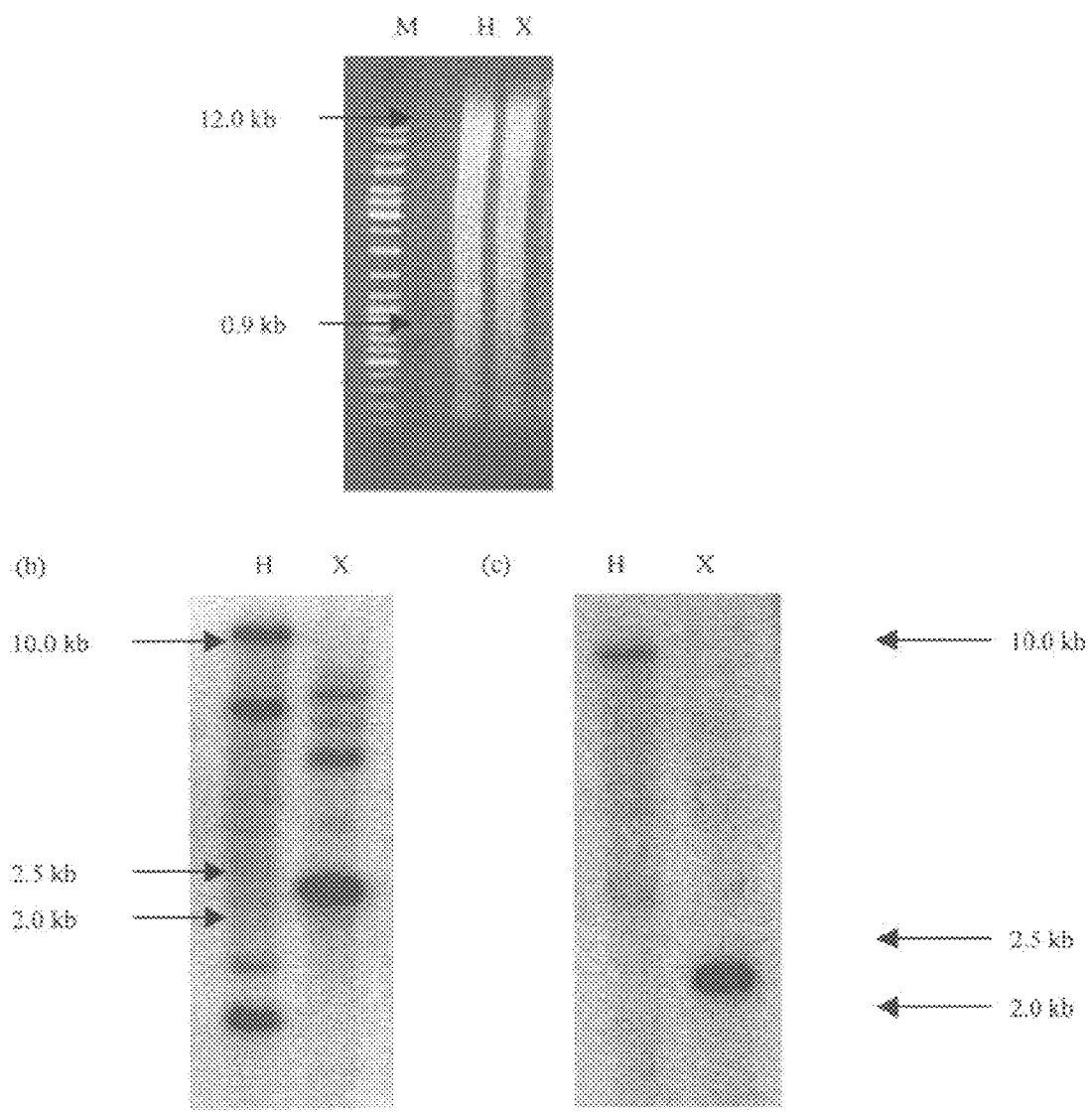
FIG. 10 gives the results of Southern analysis for determination of LS01 gene copy number in the oil palm genome. A total of 10 μg genomic DNA from oil palm leaves was digested with Hind III (Lane H) and Xba I (Lane X) prior to size fractionation on 1.0% agarose gel (10a). The digested DNA was transferred to nylon membrane and hybridized with $^{32}$P-labeled probes prepared using the entire sequence of LS01 (10b) and 3'-UTR of LS01 (10c).

Genomic Southern analysis was performed to determine the gene copy number of the oil palm LS01. The same PCR produced probes for Northern analysis were used to hybridize to the Southern blots containing genomic DNA digested with Hind III (Lane H) and Xba I (Lane X). It was observed in FIG. 10a that the entire sequence of LS01 hybridized to 4 different fragments in both lanes. However, in the membrane hybridized with the 3'-UTR probe, only one fragment was detected in each lane (FIG. 10b). It was found that these bands, 10 kb in Lane H and 2.2 kb in Lane X migrated in the same distance as one of the fragment in the membrane hybridized with the entire sequence of LS01. These results confirmed the presence of only one copy of LS01 gene in the oil palm genome.

Figure 11A:
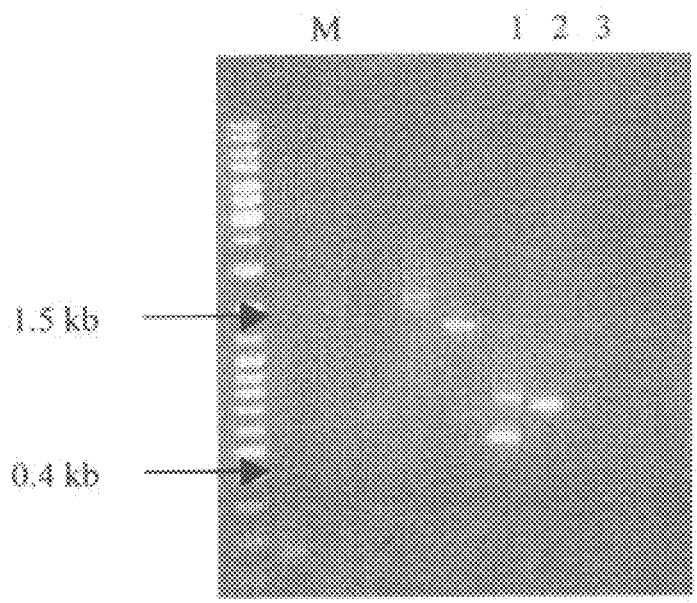
FIG. 11a shows the amplified PCR products obtained from primary PCR of GenomeWalker libraries using primers LS14 and AP1. Lane M is the DNA Ladder Mix Marker. Lanes I, 2, and 3 are the products amplified from Dra I, EcoR V, and Pvu II GenomeWalker libraries, respectively.
Figure 11B:
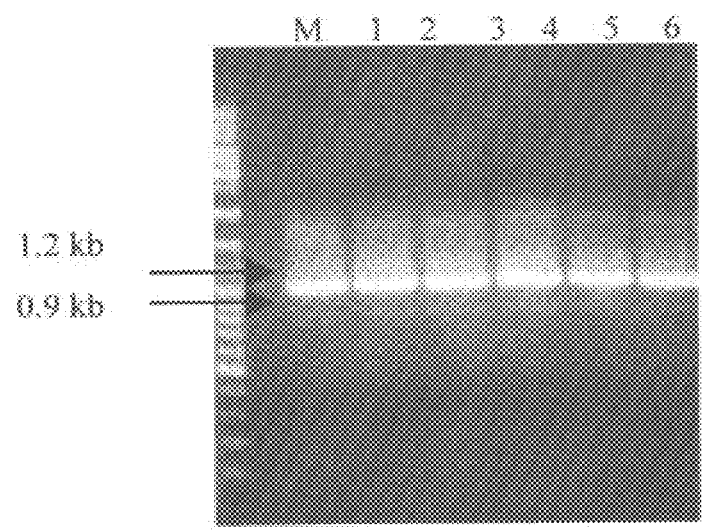
FIG. 11b shows the amplified PCR products obtained from secondary PCR of Dra I GenomeWalker library using primers LS12 and AP2. Lane M is the DNA Ladder Mix Marker. Lanes 1, 2, 3, 4, 5 and 6 are the products amplified from Dra I GenomeWalker library.

In order to obtain the 5' upstream regulatory sequence of LS01, genome-walking approach was performed using GenomeWalker kit and Advantage Genomic PCR kit from CLONTECH. In the primary PCR of GenomeWalker libraries using a 29-mer gene-specific primer, LS14 and adaptor primer, AP1, genomic fragments with different sizes were amplified from Dra I, EcoR V and Pvu II digested libraries (FIG. 11a). The largest fragment of 1.2 kb was amplified from the Dra I digested library. Whereas PCR products of approximately 800 by was amplified from both EcoR V and Pvu II libraries. Since the Dra I digested library contained the largest PCR product, it was selected as a template for secondary PCR. The library was diluted 50× and 1 μl was used in the PCR reaction with a 30-mer nested gene-specific primer, LS12, and nested adaptor primer, AP2 (5'ACTATAGGGCACGCGTGGT3'; SEQ ID NO:20). Secondary PCR using Dra I library resulted in the amplification of 1.0 kb PCR product (FIG. 11b). Since the primer LS12 located 228 by upstream of the primer LS14, smaller size of amplified genomic fragment around 1.0 kb was expected. The fragment was subsequently cloned into TOPO-pCR®II vector and the recombinant clone designated pGWLS01 was sequenced using M13 forward and reverse primer.

Sequencing result of pGWLS01 was shown in FIG. 12. A total of 932 by nucleotides upstream of the putative transcription start site coding for the promoter region. As for the 58 by nucleotides downstream of the putative transcription start site, this region overlaps with the 5'-UTR of LS01. At the expected distant 32±7 by upstream to the transcription start site, no TATA-box consensus sequence was identified (Joshi 1987). However, at position −1 to −7 upstream from the transcription start site, an initiator element (Inr) which is pyrimidine rich, PyTCANTPyPy was observed (Nakamura et al 2002). This finding revealed that the oil palm LS01 promoter is a TATA-less promoter and initiation of basal transcription could be directed by the Inr motif. The absence of TATA boxes in the majority of nuclear encoded photosynthesis genes were reported previously by Nakamura et al (2002). Their studies on 232 promoter sequences strongly suggest that TATA-independent transcription mechanisms play an important role in the regulated expression of photosynthesis nuclear genes.

Furthermore, at the distal region of the promoter, a few interesting cis-acting elements were identified. Light-responsive elements such as GATA, CCAAT, G- and I-box were commonly found in the light-responsive promoter (Arguello-Astorga & Herrera-Estrella 1998). Two separated regions that contain GATA and CCAAT motifs at position −88 and −65 relative to the transcription start site were postulated to be phytochrome-responsiveness. These motifs were also identified in the Lhcb promoter of *Lemna gibba* and other plants (Kehoe et al. 1994). In the upstream region of the promoter, a putative wound-responsive element (WUN) C AAATTCCAAA (SEQ ID NO:38) nearly identical to the WUN of pathogenesis-related gene, AAATTTCCT in potato was identified at position −464 (Matton et al. 1993). Whereas at position −699 and −878, an abscisic acid-responsive element (Knight et al. 1992) and heat-shock responsive element (Pastuglia et al. 1997) were identified, respectively. The presence of these elements indicated that the expression of LS01 gene could be regulated by environmental cues such as light, mechanical wounding, abscisic acid and heat.

Figure 13A:
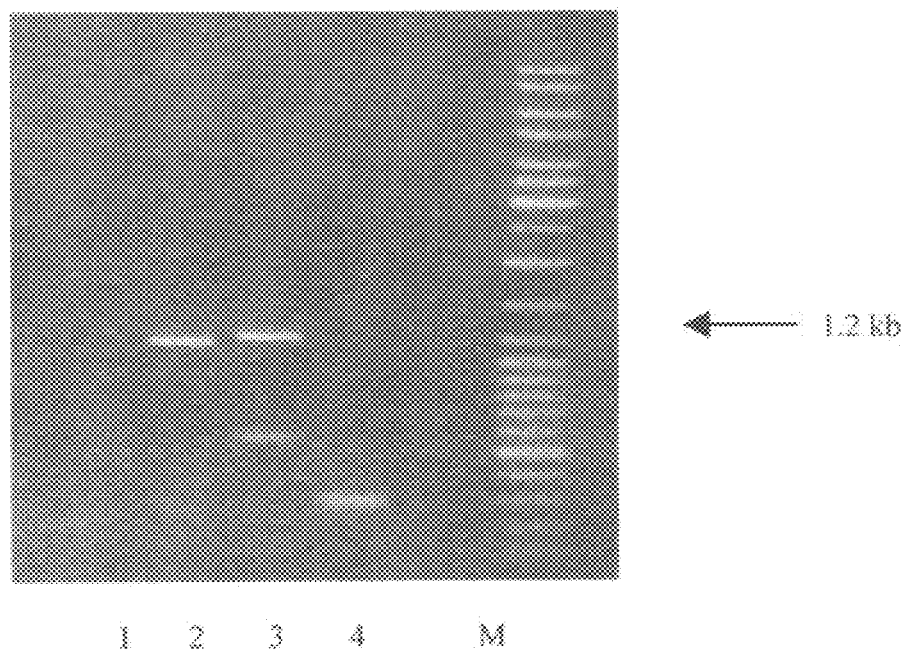
FIG. 13a shows the amplified primary PCR products from Dra I, EcoR V, Pvu 11 and Stu I GenomeWalker libraries, respectively using primers LS17 and API. Lane M is the DNA Ladder Mix Marker. Lanes 1, 2, 3 and 4 are the products amplified from Dra I, EcoR V, Pvu 11 and Stu I GenomeWalker libraries, respectively.
Figure 13B:
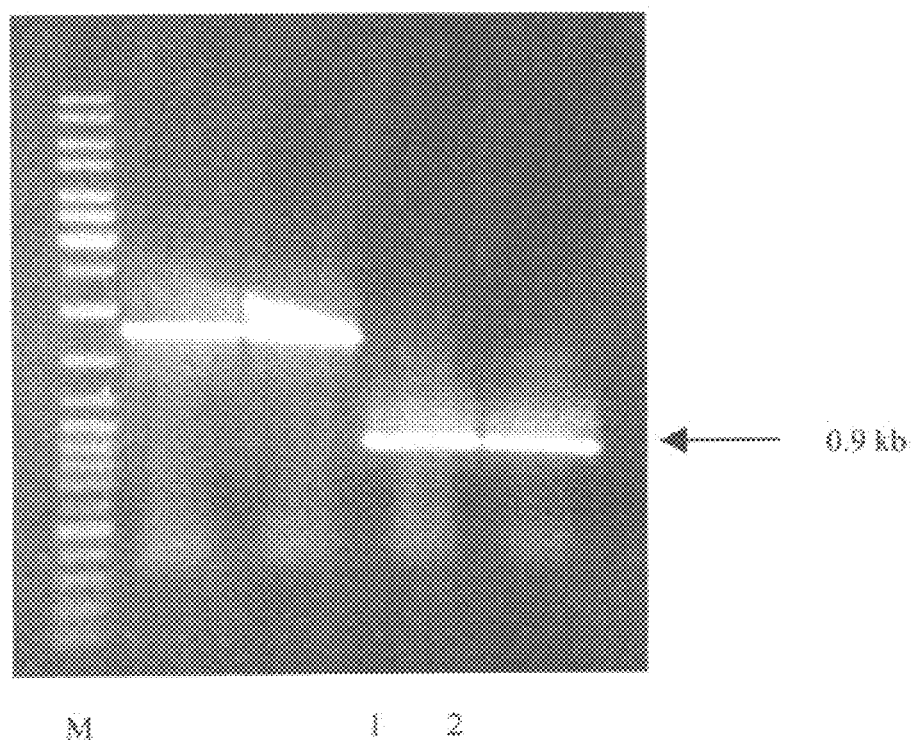
FIG. 13b shows the amplified secondary PCR products from Pvu 11 GenomeWalker library using primers LS18 and AP2. Lane M is the DNA Ladder Mix Marker. Lanes 1 and 2 are the products amplified from Pvu 11 GenomeWalker library.

GenomeWalker kit was also used to determine the presence of intron in the LS01 gene. In the primary PCR with primer LS17, an intense genomic fragment was amplified from EcoR V and Pvu II GenomeWalker libraries. No band was observed in Dra I library and only a small fragment about 0.3 kb was amplified from Stu I library (FIG. 13a). Since the fragment from Pvu II library is slightly larger than EcoR V, it was selected for secondary PCR. Further amplification of this template with nested gene-specific primer, LS18 resulted in the isolation of a 0.9 kb genomic clone (FIG. 13b). Alignment between this sequence, designated pGWLS1718 with full-length LS01 cDNA sequence was shown in FIG. 14. It was found that nucleotides upstream to the transcription start site were similar to the proximal region of LS01 promoter. Whereas a total of 508 by nucleotides downstream to the transcription start site were identical to the coding region of LS01 gene. No introns sequences were presence in this clone. Such a criterion is only observed in the Lhcb1 gene which is typically lack of introns (Arguello-Astorga & Herrera-Estrella 1998). This result further confirms that oil palm LS01 belongs to the Lhcb1 gene family.

Transient expression assay was carried out for analyzing the strength and specificity of oil palm leaf-specific promoter. A 900 by promoter which was amplified from pGWLS01 using primer LS221c and LS221d has been successfully ligated into promoterless pB1221 and pEGFP vector carrying GUS and GFP, respectively as reporter gene. Restriction analysis of the recombinant plasmids designated pLS01GUS and pLS01GFP using Sma I and Hind III was shown in FIG. 15. Digested pLS01GUS showed the presence of 5.7 kb pB1221 vector and 900 by promoter. As for pLS01GFP, fragments for vector and promoter were also observed. The size of the pEGFP vector was 4.2 kb. Analysis of the sequencing results confirmed that LS01 promoter was ligated in the correct orientation in both recombinant plasmids.

Figure 16:
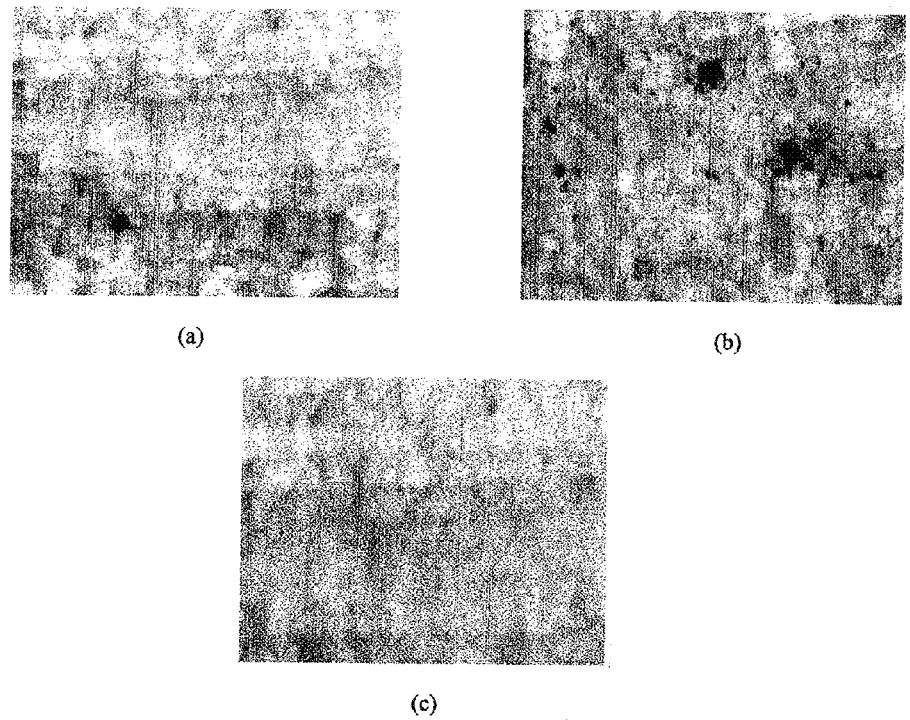
FIG. 16 shows histochemical localization of GUS expression in oil palm leaves bombarded with pLS01GUS plasmid (16a and 16b) and without plasmid (16c). The presence of blue spots were observed in the leaves bombarded with pLS01GUS (16a and 16b) but not in the negative control (16c).

In the histochemical localization of GUS expression, GUS enzyme (EC 3.2.1.31) which was encoded by the uidA locus will catalyse the cleavage of the substrate 5-bromo-4-chloro-3 indoyl glucuronide (X-Gluc). Precipitation of blue dye at the site of enzyme activity was obtained through oxidative dimerization of the indoxyl derivative. It was found that the presence of oxidative catalyst such as ferricyanide and ferrocyanide mixture could enhance this dimerization process (Jefferson et al, 1987). In the studies, 2 days of incubation in GUS staining solution resulted in the detection of 60 blue spots in the leaf tissues bombarded with pLS01GUS at 1350 psi helium pressure and 9 cm distance from macrocarrier to target tissues. Moreover, it was also observed in FIG. 16 that some blue spots could be attributed to a single blue cell (16a), but in most of the cases several adjacent cells were also stained (16b). This type of enzyme localization was also detected in the work carried out by Chowdhury et al, (1977). As for the negative control in FIG. 16c, the presence of blue spot was not observed.

Figure 17:
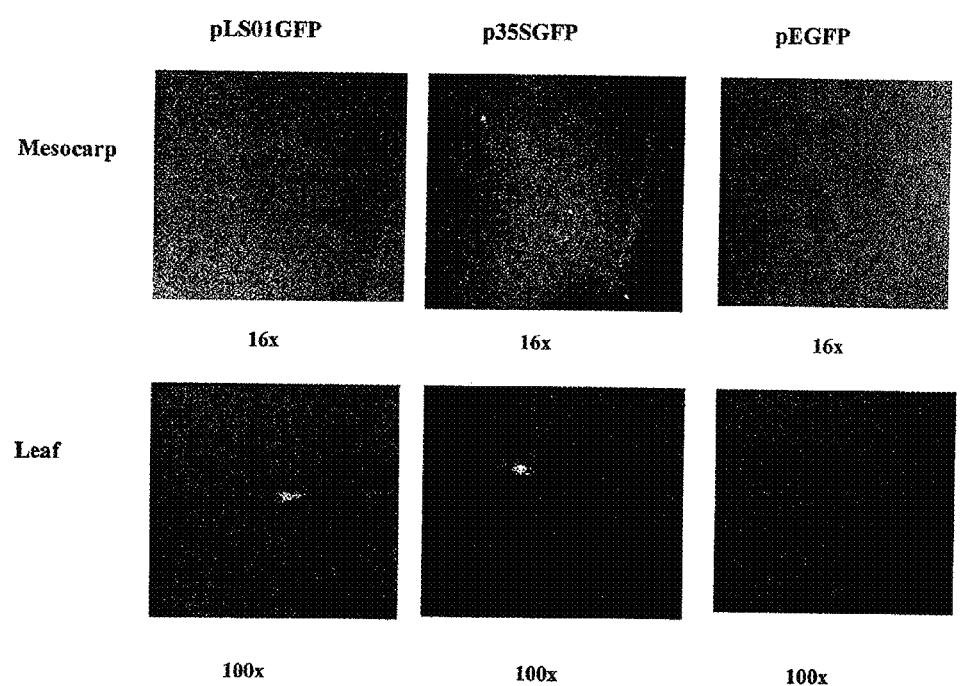
FIG. 17 provides the transient GFP expression in leaf and mesocarp tissues bombarded with different promoter-reporter gene constructs. Leaf discs and mesocarp slices were bombarded with three different plasmids: promoterless pEGFP (negative control), pEGFP driven by LS01 promoter (designated pLS01GFP) and pEGFP driven by constitutive 35S cauliflower mosaic virus promoter (p35SGFP). Expression of GFP was observed in the leaf tissues bombarded with pLS01GFP and p35SGFP. However expression of GFP was not detected in the mesocarp slices bombarded with pLS01GFP.

Specificity of LS01 promoter was further proven by the result obtained from GFP detection. Bombardment of leaf discs and control mesocarp slices with pLS01GFP showed a very promising result. Using this construct, GFP expression was detected only in the leaf but not in the mesocarp slices (FIG. 17). As for the construct driven by constitutive 35S promoter, green fluorescence spots were detected in both tissues. No expression of GFP was detected in the tissues bombarded with promoterless pEGFP.

Figure 18:
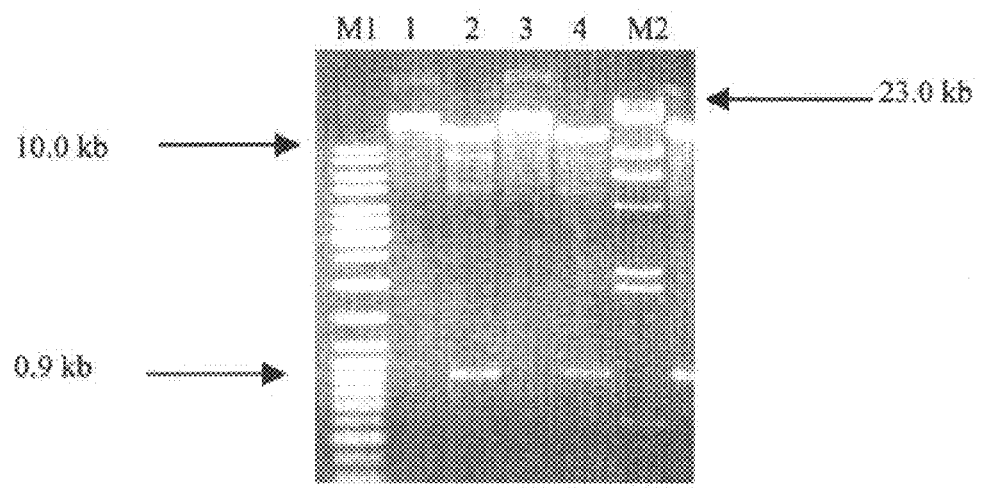
FIG. 18 shows restriction enzyme analysis of pBI101LS01 plasmid using Sma I and Hind 111. Lane M I and M2 is DNA ladder mix and λ Hind III marker, respectively. Lanes 1 and 3 are undigested pBI101LS01 plasmid. Lanes 2 and 4 are pBI101LS01 plasmid digested with Sma I and Hind 111.

For a stable integration of LS01 promoter into the Arabidopsis genome, the first step involved the construction of a suitable recombinant binary vector and cloning in E. coli. Transformation of the ligated product containing the oil palm leaf-specific promoter (LS01) and pBI101 binary vector into E. coli strain DH5α resulted in the isolation of two single bacteria colonies. The recombinant plasmids designated pBI101LS01 were then extracted from these colonies. As shown in FIG. 18, two different sizes of bands which were 12.5 kb vector and 0.9 kb LS01 fragment were observed after the pBI101LS01 plasmid was digested with Sma I and Hind 111. This analysis confirmed that LS01 has been successfully cloned into pBI101. Whereas analysis of the sequencing results showed that LS01 was ligated into pBI101 in the correct orientation.

Figure 19:
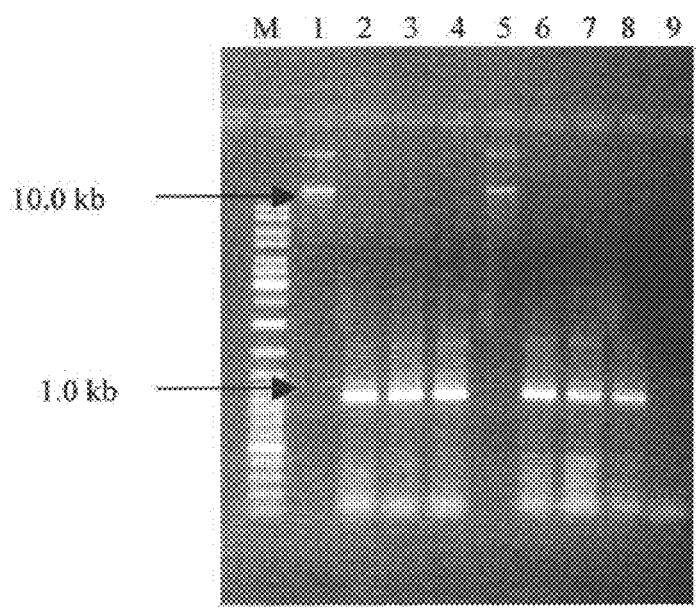
FIG. 19 provides PCR analysis of pBI101LS01 plasmid which was isolated from *Agrobacterium tumefaciens* C58 using LS01 promoter specific primers, LS221c and LS221d. Lane M is the DNA ladder mix marker. Lane I is the undigested pBI101LS01 plasmid which was isolated from *Agrobacterium* selected on LB agar plate containing 50 µg/ml kanamycin and rifampycin. Lanes 2, 3 and 4 are the PCR products amplified from plasmid in lane 1. Lane 5 is the undigested pBI101LS01 plasmid which was isolated from *Agrobacterium* selected on LB agar plate containing 50 µg/ml kanamycin. Lanes 6, 7 and 8 are the PCR products amplified from plasmid in lane 5. Lane 9 is the water negative control.
Figure 20:
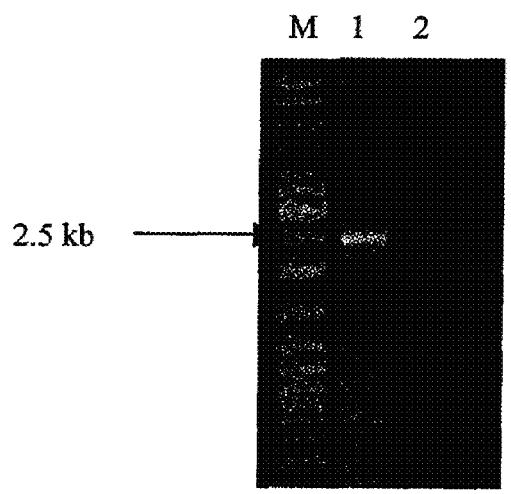
FIG. 20 shows PCR analysis of pBI101LS01 plasmid which was isolated from *Agrobacterium tumefaciens* C58 using promoter specific primer, LS221c and GUS gene specific primer, GUS-lower. Lane M is the DNA ladder mix marker. Lane 1 is the amplified PCR product for pBI101LS01 plasmid which was obtained from *Agrobacterium* selected on LB agar plate containing 50 µg/ml kanamycin and rifampycin. Lane 2 is the water negative control.

In order to enable the transfer of construct of interest into Arabidopsis, pBI101LS01 plasmid was transformed into the Agrobacterium tumefaciens strain C58 which has often been called 'nature's genetic engineer' using electroporation method. After 3 days incubation at 28° C., Agrobacterium colonies were observed in the agar plate containing kanamycin. It was found that the actual volt of 2.21 kV and time constant of 5.2 mseconds yielded bigger size colonies. Subsequently, a total of 8 transformants were grown in LB broth containing kanamycin and plasmids were prepared using QIAPREP spin miniprep kit (QIAGEN). On the other hand, glycerol stocks of the same plasmids were also restreaked on LB plate containing rifampycin and kanamycin. Plasmids were also prepared from these transformants. As shown in FIG. 19, transformants obtained from two different antibiotic selection plates showed the presence of 0.9 kb LS01 promoter fragment. This result suggested that kanamycin alone was able to select recombinant Agrobacterium. In order to verify accurately the presence of T-DNA plasmid in the transformants, PCR analysis was repeated using leaf promoter and GUS specific primers. It was observed in FIG. 20 the amplification of 2.7 kb PCR product. The expected size comprised of 1.8 kb GUS gene (Mayer et al., 2001) and 0.9 kb LS01 promoter fragment. Based on these results, the transformed Agrobacterium can be used for transforming Arabidopsis thaliana.

In planta transformation of Arabidopsis was performed via floral dip method. According to Weigel and Glazebrook (2002), this method was able to give transformant frequency of 0.1 to 1%. In the work carried out by Clough and Bent (1998), they concluded that inflorescence developmental stage and inoculation medium were the most important factors that determine the efficiency of floral dip transformation. Plants with the maximum number of unopened floral buds were the most susceptible stage for transformation. Whereas with the presence of 5% sucrose in the inoculum, a total of 1.62% transformed Arabidopsis was obtained. As for surfactant SILWET L-77, this component greatly enhances the entry of bacteria into relatively inaccessible plant tissues. In this study, plants with many immature floral bud and few opened flowers were chosen for dipping in the inoculation medium containing LB broth, 5% sucrose and 0.05% SILWET L-77. After 8 weeks on the soil, seeds were collected from the $T_1$ plant.

Figure 21:
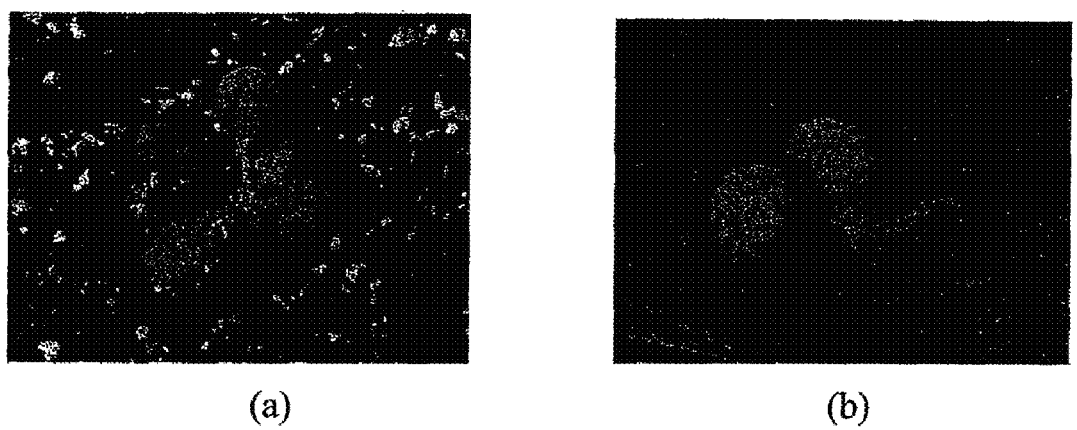
FIG. 21 shows the germination of seeds on kanamycin selection medium to identify successfully transformed *Arabidopsis thaliana* progeny. Transformant is resistant towards kanamycin and will grow into green and healthy seedlings (21a). However, non-transformant will remain as two yellowish leaves seedlings even though it was maintained on the selection medium for I month (21b).

Selection of putative transformant from $T_1$ seeds was carried out on the kanamycin selection medium. After 14 days, transformant was observed in one of the plate. The transformant was a kanamycin resistant seedling that produced green leaves and able to develop into a mature Arabidopsis plant (FIG. 21a). As for non-transformant, the seedling will only have two yellowish leaves and the growth was retarded (FIG. 21b). On the third week, the number of adult leaves of the transformed *Arabidopsis* has increased from 3 to 5 leaves. At this stage, the seedling was transplanted into soil. Seeds collected from this plant were designated as $T_2$.

Figure 22:
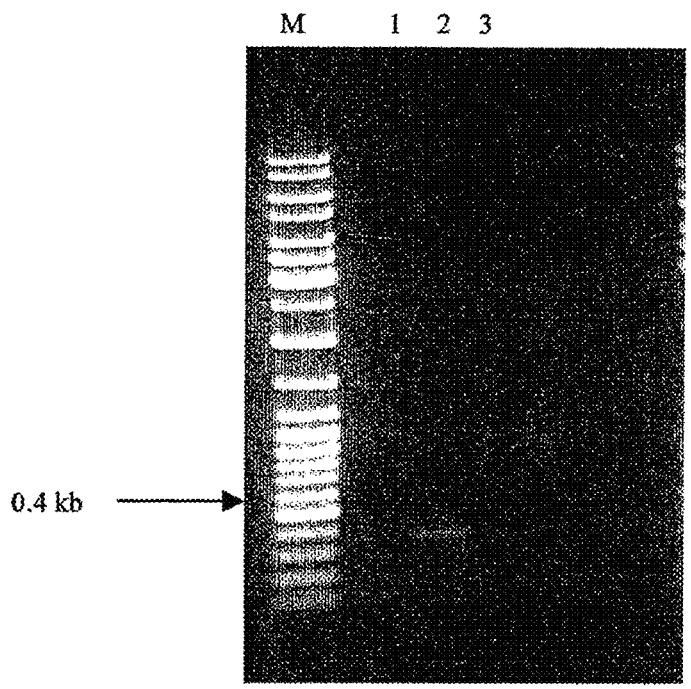
FIG. 22 shows the PCR amplification of partial GUS gene to confirm the presence of pBI101LS01 construct in the putative *Arabidopsis thaliana* transformant. Genomic DNA extracted from the leaves of transformant was amplified with primers specific for GUS gene (GUS forward, GUS3FOR and GUS reverse, GUS2REV). Lane M is the DNA ladder mix marker. A fragment of 348 bp was successfully amplified in Lane 1 and indirectly confirmed the presence of leaf-specific promoter in the transformant. GUS gene was not detected in wild type genomic DNA (Lane 2) and Lane 3 is the water negative control.
Figure 23:
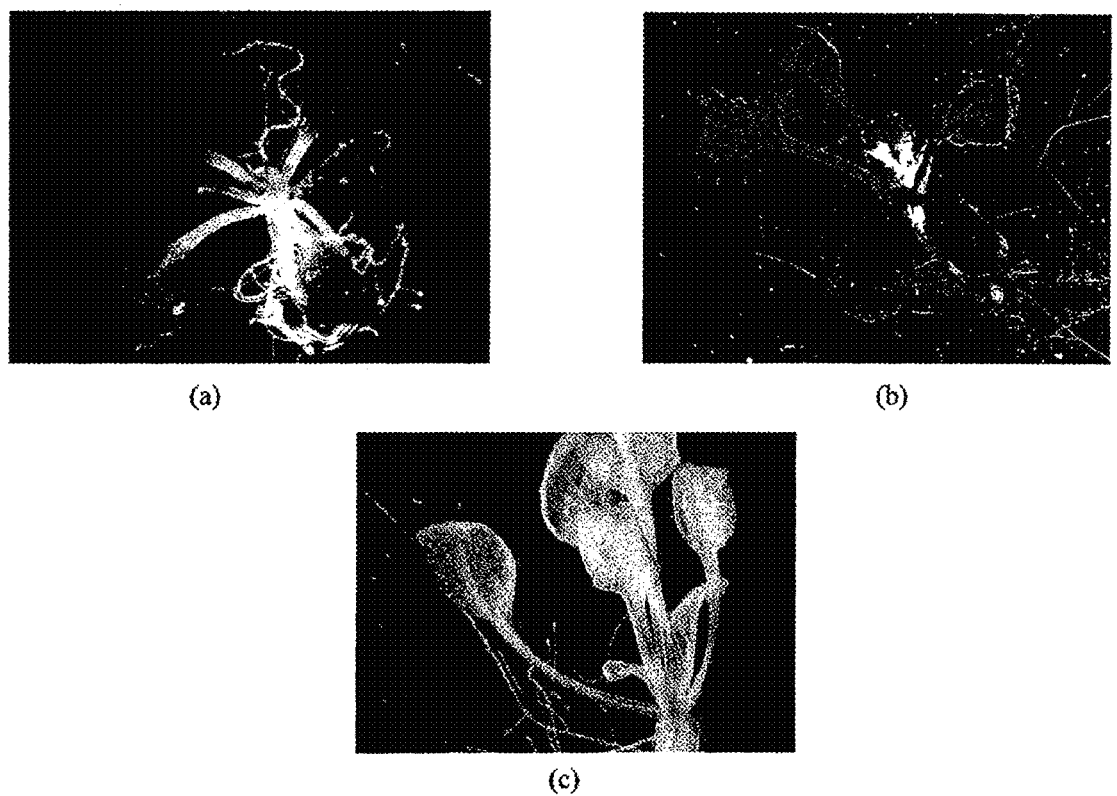
FIG. 23 provides the histochemical GUS staining of 22 days *Arabidopsis* seedlings from plants transformed with gene construct containing oil palm leaf-specific promoter and 35S CaMV constitutive promoter. Wild type plant was used as negative control. In the seedlings transformed with leaf-specific promoter, blue staining was observed only in the leaf (23a). Blue staining was detected in all the tissues (leaf, stem and root) for plant transformed with constitutive promoter (23b). Blue staining was not detected in the wild type plant (23c).

Screening of 16 plants from $T_2$ generation resulted in the isolation of one homozygous line (designated as $T_1P_1/T_2P_4$) which exhibited 100% survivor rate on the kanamycin selection medium. PCR analysis had successfully amplified a 348 by partial GUS gene from the leaf genomic DNA of this homozygous plant (FIG. 22). This further confirmed the presence of pBI101LS01 construct in the transformed plant. In addition, GUS assay of 22 days seedlings also showed the specific expression in the leaf tissue. GUS staining was observed only in the leaf tissue but not in the stem and root (23*a*). However for the plant transformed with the gene construct containing 35S constitutive promoter, all the tissues stated above were stained blue (23*b*). As for wild type plant, no blue staining was obtained (23*c*).

Based on the results from transient expression assay and stable transformation in the *Arabidopsis*, it can be concluded that the LS01 promoter was able to drive the expression of transgenes specific to the leaf tissue. Furthermore, successful transformation of this promoter into the *Arabidopsis* also showed that it can be used in the heterologous plant system.

EXAMPLES

Example 1

Amplification of Lhcb Gene Via Reverse Transcription and Polymerase Chain Reaction (RT-PCR) Approach First strand cDNA was synthesized from leaf mRNA in 25 µl reaction containing 5 µg leaf mRNA, 4 µl 5× first strand buffer, 2 µl 0.1 M DTT, 5 µl 2 mM dNTP and 1 µl SUPER-SCRIPT II reverse transcriptase (200 U/µl) (Gibco BRL Life Technology Inc. New York, USA) at 42° C. for 1 hour. The solution was phenol-chloroform extracted, ethanol precipitated and the pellet was dissolved in 25 µl sterile water. The cDNA was subjected to RNA hydrolysis using 12.5 µl 0.15 N NaOH and 1 µl 0.5 M EDTA at 68° C. for 15 min. This was followed by neutralization of the reaction by addition of 12.5 µl Tris-HCl, pH 8.0; 12.5 µl N HCl and 17.3 µl 7.5 M ammonium acetate prior to ethanol precipitation. The cDNA pellet was dissolved in 25 µl sterile water and the concentration of cDNA was determined using ethidium bromide plate.

PCR was carried out with the presence of degenerate primers [CAB(R)-5'CNGGRTCNGCDATRTGRT3' (SEQ ID NO:9) and CAB(F)-5'GCNGAYCCNGARACNTTY3' (SEQ ID NO:8)] which were designed based on the conserved region of known chlorophyll a/b binding protein genes from maize, wheat and rice. The 50 µl PCR mixture contained 1 µl cDNA (50 ng), 5 µl 10× buffer, 1 µl d 10 mM dATP, 1 µl 10 mM dCTP, 1 µl 10 mM dGTP, 1 µl 10 mM dTTP, 2 µl 15 µM CAB(R), 2 µl 15 µM CAB(F), 5 µl 25 µM $MgCl_2$, 30.5 µl sterile water and 0.5 µl AMPLITAQ DNA polymerase (5 U/µl). The PCR reaction was placed in the Perkin Elmer 9700 thermo cycler with the following conditions: 94° C., 5 min for 1 cycle; followed by 94° C., 1 min; 43° C., 1 min and 72° C., 1 min 30 sec for 40 cycles and finally 72° C., 10 min for 1 cycle. The expected fragment was purified using QIAQUICK Gel Extraction Kit (QIAGEN), cloned into TOPO-pCR®II vector from TOPO-TA Cloning Kit (Invitrogen) before subjected to automated sequencing with ABI 377 PRISM. Analysis of the nucleotide sequences were performed using DNAsis Max version 1.0 prior to database homology search.

Example 2

Screening of Leaf cDNA Library with cDNA Probe Generated from T-PCR

A total of 200,000 plaques from leaf cDNA library constructed in Uni-ZAP XR vector (Stratagene) were plated based on Sambrook et al (1989) and plaque lift was performed as described by Siti Nor Akmar et al (1995). The plaques lifted membranes were first treated with denaturation buffer (0.5 N NaOH, 1.0 M NaCl) for 10 min, followed by neutralization buffer (0.5 M Tris-HCl, pH 8.0; 1.5 M NaCl) for 5 min and 2×SSC for 5 min prior to optimal crosslinked with UV light.

Prehybridization of the membranes were carried out at 65° C. in 5×Denhardt's solution (1×Denhardt's solution is 0.02% each Ficoll 400, bovine serum albumin and polyvinylpyrrolidone), 5×SSPE (1×SSPE is 0.18 M NaCl, 10 mM $NaH_2PO_4$, pH 7.5, 1 mM EDTA), 0.5% SDS and 100 µg/ml denatured herring sperm DNA. Hybridization of the membranes was performed using the same hybridization buffer with the presence of $^{32}$P-labelled pRTLS01 at 65° C. The probe was labeled with $^{32}$P-dCTP using MEGAPRIME DNA Labeling Kit from Amersham Pharmacia Biotech. After overnight hybridization, the membranes were washed at 65° C. with 4×SSPE, 0.1% SDS; followed by 2×SSPE, 0.1% SDS and 0.5×SSPE, 0.1% SDS. These membranes were then exposed to x-ray film for 24 hours at −80° C.

Based on the signal detected on x-ray film, putative plaques were cored out and placed into SM buffer (100 mM NaCl, 10 mM $MgSO_4.7H_2O$, 0.05 M Tris-HCl and 0.01% gelatin) containing 0.3% chloroform. The phage lysate was subjected to PCR analysis with the presence of primer T7 and gene-specific primers. The PCR conditions were as follows: 95° C., 5 min and 80° C., 45 min for 1 cycle; followed by 95° C., 1 min; 60° C., 1 min and 72° C., 1 min 30 see for 30 cycles and 1 cycle of final extension at 72° C. for 10 min. Amplified products were visualized on 1.2% agarose gel.

Recombinant phage was in vivo excised according to the manufacturer's instruction (Stratagene). The purified pBluescript phagemid was digested with EcoR I and Xho I to confirm the length of cDNA insert.

Example 3

Rapid Amplification of 5'-cDNA Ends (5'-RA CE)

A full-length sequence of chlorophyll a/b binding protein gene was isolated via 5' RACE using SMART RACE cDNA amplification Kit and Advantage 2 PCR Kit from CLONTECH, Laboratories, Inc., USA. The reaction for first strand cDNA was initiated by incubation of 1 µg total RNA from leaf with 1 µl 5'-CDS primer, 1 µl SMART II A oligo and 2 µl sterile water at 70° C. for 2 min. The reaction was immediately cooled on ice prior to addition of 2 µl 5× first strand buffer, 1 µl 20 mM DTT, 1 µl 10 mM dNTP mix and 1 µl reverse transcription PowerScript. This was followed by incubation at 42° C. for 1.5 hours. The reaction was stopped by addition of 200 µl Tricine-EDTA buffer and incubation at 72° C. for 7 min.

A total of 2.5 µl single stranded 5'-RACE Ready cDNA was added to the PCR mixture containing 34.5 µl PCR grade water, 5 µl 50× Advantage 2 polymerase buffer, 5 µl 10×UPM primer and 1 µl 10 µM gene-specific primer, LS10 (5'TAAT- GCACACCACGCCAACAATTTCAATTC3'; SEQ ID NO:12) which was designed based on the sequence of pRTLS01. The PCR reaction was carried out using Perkin Elmer 9700 thermo cycler with the following conditions: 94° C., 5 sec; 68° C., 10 sec and 72° C., 3 min for 25 cycles. The expected fragment was purified, cloned into TOPO-pCR®II vector from TOPO-TA Cloning Kit (Invitrogen) before subjected to automated sequencing with ABI 377 PRISM. Analysis of the nucleotide sequences were performed using DNA-SIS Max version 1.0.

Example 4

Northern Blot Analysis

Total RNA was extracted from various tissues of oil palm according to the method of Rochester et al. (1986).

Two different fragments containing complete nucleotide sequence and 3' untranslated region (3'-UTR) of chlorophyll a/b binding protein gene were used as probes in the Northern and Southern analysis. The complete nucleotide sequence of LS01 was generated through amplification of plasmid LS10.3 with primer LS10 (5'TAATGCACACCACGCCAA-CAATTTCAATTC3'; SEQ ID NO:12) and LS15 (5'GCAC-CTACCCAACAGCATTTCCATTGG3'; SEQ ID NO:16). Whereas 3'-UTR region was amplified using LS10 and LS11 (5'GCCTGGCAACCTTAATTAATTTGGTGCTTAG3'; SEQ ID NO:13) primer pair. The expected fragments were purified using QIAQUICK Gel Extraction Kit (QIAGEN) and labeled with $^{32}$P-dCTP using MEGAPRIME DNA Labeling Kit from Amersham Pharmacia Biotech.

Northern blot analysis has been carried out according to the method of McMaster & Carmichael (1977) and Kroczek & Siebert (1990). In this study, 5 µg of total RNA was heat denatured at 55° C. for 15 min in 18 µl GFP mixture containing 78% (v/v) deionized formamide, 16% deionized glyoxal and 10 mM sodium phosphate buffer. After heat denaturation, the RNA was cooled immediately on ice prior to electrophoresis on 1.2% agarose gel with 40 mM 1×TAE, pH 7.2 as electrophoresis buffer. The RNA was transferred to HYBOND-N⁺ membrane (Amersham Pharmacia Biotech) via a vacuum blotter (60 psi, 6 hours) with the presence of 20×SSC as transfer buffer.

Prehybridization of the membrane was performed at 65° C. for 4 hours in 5×SSC (1×SSC is 0.15 M NaCl, 15 mM trisodium citrate), 5×Denhardt's (1×Denhardt's is and 0.02% each Ficoll 400, bovine serum albumin and polyvinylpyrrolidone), 0.5% SDS100 µg/ml denatured herring sperm DNA. This was followed by overnight hybridization of the membrane with $^{32}$P-labeled probe at 65° C. Washing of the membrane was performed with 4×SSC/0.1% SDS at 65° C. for 15 min, followed by 2×SSC/0.1% SDS at 65° C. for 15 min. Exposure to x-ray film was carried out at −80° C. for 48 hours.

Example 5

Southern Blot Analysis

Genomic DNA was extracted from oil palm spear leaves according to the method of Doyle & Doyle (1990).

A total of 20 µg genomic DNA was digested with Hind III and Xba I. The digested products were size fractionated on 1.0% agarose gel at 100 v for 5 hours in 1×TAE, pH 7.9. This was followed by immobilization of the DNA onto nylon membrane via vacuum blotting of the gel at 60 psi for 1 hour with the presence of 0.4 N NaOH as transfer buffer. At the end of the process, the membrane was rinsed with 2×SSC prior to UV-crosslinking. Hybridization and washing of the blot was performed as stated above for Northern blot analysis.

Example 6

Promoter Isolation

Leaf-specific promoter was isolated following the standard protocol stated in the manual of Universal GenomeWalker Kit and Advantage Genomic PCR Kit from CLONTECH Laboratories, Inc. Two antisense gene-specific primers, designated LS14 (5'GTGTCCCACCCATAGTCACCGGG-GAATTC3'; SEQ ID NO:15) and LS12 (5'GATGATGCCT-TGGAGATGGGAGCGGTGATC3'; SEQ ID NO:14) were designed based on the 5'-terminal of the coding region of LS01 and within 5'-UTR of LS01, respectively. A total of four GenomeWalker libraries were obtained through digestion of 2.5 µg leaf genomic DNA with Dra 1, EcoR V, Pvu 11 and Stu I prior to ligation with the GenomeWalker adaptor. An aliquot of 12 µl of these libraries were used in the adaptor primer, AP2 (5'ACTATAGGGCACGCGTGGT3'; SEQ ID NO:20), supplied in the kit. PCR conditions were carried out as primary PCR reaction with the presence of antisense gene-specific primer, LS12, and adaptor primer, AP1 (5'GTAATACGACT-CACTATAGGGC3'; SEQ ID NO:19) provided with the kit. This was followed by secondary PCR of 50× diluted primary library with antisense nested gene specific primer, LS14 and recommended in the GenomeWalker Kit manual using Perkin Elmer 9700 thermo cycler. The expected band was purified from agarose gel using QIAquick Gel Extraction Kit (QIAgen), cloned into TOPO-pCR®II vector from TOPO-TA Cloning Kit (Invitrogen) prior to sequencing using M13 reverse and forward primers.

Genome walking approach was also used to study the structure of LS01 gene. Primary PCR of the GenomeWalker libraries was carried out with the presence of antisense gene-specific primer, LS17 (5'CGAAGTTGGTGGCGTAGGC-CCAAGCATTG3'; SEQ ID NO:17) from 3'-terminal of the coding region of pLS01 and primer AP 1. Followed by secondary PCR with antisense nested gene specific primer, LS18 (5'CTCTGAGCATGGATCAAGCTCGGGTTGCC3'; SEQ ID NO:18) from 5'-terminal of the coding region of pLS01 and primer AP 2. The expected band was purified, cloned and sequenced as above.

Example 7

Cloning of the Leaf-Specific Promoter into pBI221 and pEGFP Vector

Leaf specific promoter (922 bp) was amplified from plasmid pGWLS01 using sense and antisense primer. The sense primer, LS221c (5'CCCAAGCTTCCATATCTGGCTCG3'; SEQ ID NO:21) was introduced with Hind III site at the 5' end. As for antisense primer, LS221d (5'TC-CCCCGGGCAATGGAAATGCTG3'; SEQ ID NO:22), 5' end was introduced with Sma I site. These primers, 2 µl of 15 µM stock, were used to amplify the promoter in 50 µl PCR reaction contained 4 µl dNTP (10 mM each), 250 ng plasmid pGWLS01, 5 µl 10× buffer, 5 µl 25 mM MgCl$_2$ and 2.5 U AMPLITAQ DNA Polymerase from Perkin Elmer. PCR conditions were as follows: 95° C., 5 min for 1 cycle; followed by 95° C., 1 min; 56° C., 1 min and 72° C., 1 min 30 sec for 30 cycles and 1 cycle of final extension at 72° C. for 10 min. The PCR product was purified from primers, nucleotides, polymerases and salts using QIAQUICK PCR Purification column from QIAGEN. Plasmid pBI221 carrying GUS as reporter gene and promoterless plasmid, pEGFP carrying GFP as reporter gene were prepared using QIAPREP Miniprep kit from QIAGEN. Fragment of LS01 promoter, plasmid pBI221 and pEGFP were digested first with Sma I (Fermentes) at 30° C. for 6 hours. Digestion with second restriction enzyme, Hind III (Fermentes) was performed at 37° C. for 16 hours. The digested products were analyzed on 1.0% agarose gel and expected fragments were purified from the agarose gel using QIAQUICK Gel Extraction Kit from QIAGEN.

Digested LS01 promoter and promoterless pBI221 at a molar ratio of 4:1 were incubated at 50° C. for 5 min. After immediate cooling, the vector and insert mixture were added into ligation mixture containing 1.5 µl 10× ligase buffer and 1.5 µl T4 DNA ligase (1 U/µl) prior to overnight incubation at 16° C. Ten microliters of the ligation mixture were used for transformation with competent cell of *E. coli* DH5α as described by Siti Nor Akmar Abdullah (1999). Blue/white selection of recombinant clones were carried out on LB plate containing 40 µl of 20 mg/ml 5-bromo-4-chloro3-indolyl-β-D-galactopyranoside (X-gal) and 40 µl of 20 mg/ml isopropyl β-Dthiogalactopyranoside (IPTG). Plasmid of the recombinant clone, designated pLS01GUS was prepared using QIAPREP Spin Miniprep Kit (QIAGEN) and digestion with restriction enzymes Sma I and Hind III was performed to confirm the insert size. Lastly, the plasmid was sequenced using M 13F (5'GTAAAACGACGGCCAG3'; SEQ ID NO:24) and M13R (5' CAGGAAACAGCTATGAC3'; SEQ ID NO:25) primers. Cloning of the digested LS01 promoter into promoterless pEGFP was also carried out as above and the recombinant clone, pLS01GFP was sequenced using EGFPN primer (5'CGTCGCCGTCCAGCTCGACCAG3'; SEQ ID NO:23).

Example 8

Promoter Analysis Via Histochemical GUS Assay and GFP Detection

Preparation of Tissue Slices

Oil palm green leaves were collected from seedling palm in MPOB nursery. The tissues were soaked in RBS for 15 min before subjecting to surface sterilization using 20% of CLOROX for 15 min in the laminar flow. The leaves were rinsed twice with sterile water, cut into segments of 1.0 cm² and were flattened on Murashige and Skoog medium (Duchefa, Biochemicals Plant Cell and Tissue Culture, Haarlem, Netherlands) with the lower epidermis facing upward. Leaf discs were kept at 28° C. for 24 hours and were illuminated before and after bombardment with chimeric gene construct.

Preparation of Gold for Particle Bombardment

A total of 1 ml absolute ethanol was added to 0.06 g of 1.0 micron gold particles. The mixture was mixed by vortexing at high speed. After centrifugation at 10,000 g for 1 min, the supernatant was removed from the gold pellet. These sterilization steps were repeated for 3 times. At the final sterilization, 1 ml sterile water was added to the gold pellet. Sonication of the gold pellet was repeated 3 times before the gold was resuspended in 1 ml sterile water. The gold can be stored at −20° C. for up to 6 months.

Precipitation of DNA onto Gold Microprojectiles

An approximately 10 µg of plasmid pLS01 GUS was added to 2 µg of gold particles in a microcentrufuge tube. While vortexing, 100 µl 2.5 M calcium and 40 µl 0.1 M spermidine was added. The mixture was vortexed for 3 min prior to centrifugation at 10,000 g for 1 min. The supernatant was removed and the microcarrier was resuspended in 65 µl absolute ethanol. The DNA-coated microcarrier can be kept at ±20° C. until used.

Microprojectile Bombardment

Leaf discs were bombarded with gene construct using the BioRad (Hercules, Calif., USA) PDS-1000/Helium-driven Particle Delivery System. Before bombardment, the machine chamber, rupture disc, stopping screen, macrocarrier, macrocarrier holder and red caplugs were sterilized with absolute ethanol. An aliquot of 8 µl DNA-coated macrocarrier was loaded onto the center of the macrocarrier and air dried for 10 minutes. The leaf discs were bombarded using the following conditions: 1350 psi helium pressure with 9 cm distance from macrocarrier to target tissues. As for mesocarp slices, bombardment was performed at 1550 psi with 9 cm distance from macrocarrier to target tissues. Leaf discs bombarded without plasmid DNA were used as negative control in GUS assay. Whereas in GFP, leaf discs and mesocarp slices bombarded with promoterless pEGFP were used as negative control. After bombardment, the leaf tissues were incubated for 24 hours at 28° C. in the light prior to GUS assay and GFP detection.

Histochemical GUS Assay

GUS activity was measured histochemically following the method described by Jefferson et al. (1987). The leaf tissues were incubated in filter-sterilized GUS staining buffer (0.1 M sodium phosphate buffer, pH 7.0; 5 mM potassium ferrocyanide, 5 mM potassium ferricyanide, 1 mg/ml 5-bromo-4-chloro-3-indoyl glucuronide/X-Gluc, 0.2% Triton X-100 and 10 mM EDTA) for up to 2 days at 37° C. in the dark. After staining, the tissues were fixed in fixative mix (10% formaldehyde, 50% ethanol and 5% glacial acetic acid) and the leaves chlorophyll was removed using 80% ethanol. The presence of blue spots were observed using LEICA QF550W System.

Detection of Green Fluorescent Protein (GFP)

Microscopic detection of GFP was carried out using LEICA MZ 12.5 microscope with blue light. Image of the GFP was captured using Image Manager 50 computer software.

Example 9

Promoter Analysis Using *Arabidopsis thaliana* (Model Plant System)

Preparation of pB1101LS01 Construct

Fragment of leaf-specific promoter from plasmid pGWLS01 and promoterless binary vector pBI101 (at a molar ratio of 13:1) which have been digested with Sma I and Hind III were heat treated at 55° C. for 5 min. This was followed by immediate cooling and addition of ligation mixture containing 1.5 µl 10× ligase buffer and 1.5 µl T4 DNA ligase (1 U/µl) prior to overnight incubation at 16° C. Fifty microliters of the ligation mixture were then used to transform competent cell *E. coli* DH5α and selection of recombinant clones were carried out on Luria-Bertani (LB) plate containing 50 µg/ml kanamycin. Plasmid of the recombinant clone, designated pBI101LS01 was prepared using QIAPREP spin miniprep kit (QIAGEN) and digestion with restriction enzymes Sma I and Hind III was performed to confirm the insert size. Lastly, the plasmid was sequenced using M13F and M13R primers.

Electroporation

A total of 100 ng binary plasmid pBI101LS01 was mixed on ice with 100 µl competent cell of *Agrobacterium tumefaciens* strain C58 in a prechilled Gene Pulser Cuvette (0.2 cm electrode gap). The mixture was subjected to electroporation using Electroporator Gene Pulser®II (Bio-Rad) with the following conditions: capacitance: 1.0 voltage: 2.2 kV and time constant: 5 to 10 mseconds. Immediately after electroporation, 1 ml of LB broth was added to the cuvette prior to incubation at 28° C. for 4 hours. The culture was incubated without shaking for the first 2 hours and continued by gentle shaking at 150 rpm for the following 2 hours. After incubation, the cells were collected by centrifuging briefly at 4000 rpm for 1 min. The pellet was resuspended in 40 μl of LB broth and the cells were plated on LB plate containing 50 μg/ml kanamycin. The plate was incubated for 3 days at 28° C. and PCR was performed using primers specific for leaf promoter and GUS gene (GUS-lower, 5'CATTGTTTGC-CTCCCTGCTGCGGTT3'; SEQ ID NO:26) to verify the presence of the recombinant binary vector, pBI101LS01 in the *Agrobacterium*.

Growing of the *Arabidopsis* Plant

Seeds from *Arabidopsis thaliana* ecotype Columbia were germinated and grown to flowering stage in a flower pots filled with a soil mixture of two-thirds Steven Dutch potting mix and one-third vermiculite in a growth chamber. The growth conditions were 16 hours lights (80-100 μmol/m$^2$) at 22° C./8 h dark at 20° C., with a relative humidity of 75%. In order to obtain more floral bud per plant for dipping, primary inflorescences were clipped to encourage the emergence of secondary bolts.

In Planta Transformation Via Floral Din

A single colony of *Agrobacterium tumefaciens* strain C58 harboring the binary plasmid pBI101LS01 was grown overnight at 28° C. with shaking (220 rpm) in LB broth containing 50 μg/ml kanamycin. The overnight cultures were diluted to 1:10 using LB broth and grown for approximately 8 hours to obtain OD$_{600}$ of 0.6-0.8. Cells were harvested by centrifugation at 5000 rpm for 15 min. The pellet which was pink in color was then resuspended in 5% (w/v) sucrose. The culture was transferred to a square container and SILWET L-77 was added to 0.05% (v/v). Plants were inverted into this suspension and dipped for 10 seconds. Plants were then removed and the flower pots were enclosed with plastic bags. Top of the plastic bags were closed with paper clip for 2 days to maintain high humidity. After 48 hours, the paper clip was removed and the plants were grown under normal growing conditions. The plant which was designated as $T_1$ were grown to maturity and harvested when the siliques were brown and dry.

Screening and Selection of Putative Transformant

Harvesting of Transgenic Seeds

Seven weeks after floral dip, putative transgenic seeds were harvested by gentle pulling of dry siliques through fingers over a piece of clean paper. The seeds were sieved to remove the pod materials. Clean seeds were stored in the EPPENDORF tube and kept at 22° C. in the dessicator.

Sterilization of Transgenic Seeds

The seeds were suspended in sterile water containing 1% TWEEN 20 (v/v) in an EPPENDORF tube. The seeds were vortexed, centrifuged and rinsed with sterile water 3 times prior to soaking in 25% Clorox for 20 minutes. Clorox was then removed by washing the seeds with sterile water 3 times. Lastly the seeds were subjected to surface sterilization with 70% ethanol for 1 minute. The seeds were rinsed again with sterile water before it can be used for selection.

Selection for Homozygous Line Carrying Leaf-Specific Promoter

Sterilized seeds were plated on Murashige and Skoog medium supplemented with 50 μg/ml kanamycin. The selection plates were cold-treated at 4° C. in the dark for two days to promote the uniform germination of seeds. The plates were then transferred to 22° C. under continuous fluorescent light illumination. After about 3 weeks, 16 kanamycin-resistant seedlings were transplanted into soil. These $T_2$ generation plants were grown to maturity and individually harvested. Seed sterilization and screening were repeated for these 16 plants. Only those $T_3$ generation seedlings that shown 95% and above survivor rate on the kanamycin selection plate were considered as homozygous line. These plants were then transplanted into soil for seeds collection.

PCR Analysis of Transformant

Genomic DNA was extracted from *Arabidopsis* leaves carrying leaf-specific promoter according to the method described by Doyle and Doyle (1990). PCR amplification was performed using primers specific for the GUS gene which are GUS3FOR (5'TGACGCATGTCGCGCAAGAC3'; SEQ ID NO:27) and GUS2REV (5'ATCCTTTCGCACG-TAAGTCC3'; SEQ ID NO:28). In this study, genomic DNA from wild type *Arabidopsis* was taken as negative control.

Histochemical GUS Assay of Transformant

GUS activity was measured histochemically following the method described by Jefferson et al. (1987). The whole plant of *Arabidopsis* seedling (22 days) carrying leaf-specific promoter were incubated in filter-sterilized GUS staining buffer (0.1 M sodium phosphate buffer, pH7.0; 1 mg/ml 5-bromo-4-chloro-3-indoyl-glucuronide/X-gluc and 0.2% Triton X-100) overnight at 37° C. in the dark. After staining, chlorophyll was removed from the plant using 70% ethanol. The presence of blue precipitate were observed using NIKON SMZ800 Stereomicroscope. Blue deposits due to GUS activity in the transformant was compared with *Arabidopsis* carrying 35S constitutive promoter and also wild type plant.

References

Anderson, D. M., Hudspeth, R. L., Hobbs, S. L. & Grula, J. W. 1993. Chlorophyll a/b binding protein gene expression in cotton. *Plant Physiol.* 102: 1047-1048.

Arguello-Astorga, G. & Herrera-Estrella, L. 1998. Evolution of light-regulated plant promoters. *Annu. Rev. Plant Physiol. Plant Mol. Biol.* 49: 525-555.

Buetow, D. E., Chen, H., Erdos, G. & Lee, S. H. Y. 1988. Regulation and expression of the multigene family coding light-harvesting chlorophyll a/b binding proteins of photosystem 11. Dlm. Govindjee, Bohnert, H. J., Bottomly, W., Bryant, D. A., Mullet, J. E., Ogren, W. L., Pakrasi, H. & Somerville, C. R. (pnyt.). *Molecular Biology of Photosynthesis*, hlm. 283-319. New York: Kluwer Academic Publishers.

Chinn, E., Silverthorne, J. & Hohtola, A. 1995. Light-regulated and organ-specific expression of types 1, 2, and 3 light-harvesting complex b mRNAs in *Ginkgo biloba*. *Plant Physiol.* 107: 593-602.

Chowdhury, M. K. U., Parveez, G. K. A. & Norihan, M. S. 1997. Evaluation of five promoters for use in transformation of oil palm (*Elaeis guineensis* Jacq.). *Plant Cell Reports.* 16: 277-281.

Clough, S. J. & Bent, A. F. 1998. Floral dip: a simplified method for *Agrobacterium*-mediated transformation of *Arabidopsis thaliana*. *Plant J.* 16(6): 735-743.

Demmin, D. S., Stockinger, E. J., Chang, Y. C. & Walling, L. L. 1989. Phylogenetic relationships between the chlorophyll a/b binding protein (CAB) multigene family: an intra and interspecies study. *J. Mol. Evol.* 29: 266-279.

Doyle, J. J. & Doyle, J. L. 1990. Isolation of plant DNA from fresh tissue. FOCUS 12(1):13-15.

Fernandez, S. V., Cerdan, P. D. & Staneloni, R. J. 1995. Isolation and characterization of a cluster containing six Lhcb I gene from potato (*Solanum tuberosum*). *Plant Physiol.* 108: 1342.

Jansson, S. & Gustafsson, P. 1990. Type I and Type 11 genes for the chlorophyll a/b-binding protein in the gymnosperm *Pinus sylvestris* (Scots pine): cDNA cloning and sequence analysis. *Plant Mol. Biol.* 14: 287-296.

Jefferson, R. A., Kavanagh, T. A. and Bevan, M. V. 1987. GUS fusions: glucuronidase as a sensitive and versatile gene fusion marker in higher plants. *EMBO J.* 6(13): 3091-3097.

Joshi, C. P. 1987. An inspection of the domain between putative TATA box and translation start site in 79 plant genes. *Nucleic Acids Res.* 15(16): 6643-6653.

Kehoe, D. M., Degenhardt, J., Winicov, 1. & Tobin, E. M. 1994. Two 10 by regions are critical for phytochrome regulation of a *Lemna gibba* Lhcb gene promoter. *Plant Cell* 6:1123-1134.

Knight, M. E., Ray, J. A. & Schuch, W. 1992. Isolation of a gene from maize encoding a chlorophyll a/b binding protein. *Plant Mol. Biol.* 19: 533-536.

Kroczek, R. A. & Siebert, E. 1990. Optimization of Northern analysis by vacuum blotting, RNA-transfer visualization, and ultraviolet fixation. *Anal. Biochem.* 184: 90-95.

Matton, D. P., Prescott, G., Bertrand, C., Camirand, A. & Brisson, N. 1993. Identification of cis-acting elements involved in the regulation of the pathogenesisrelated gene STH-2 in potato. *Plant Mol. Biol.* 22: 279-291.

Mayer, A., Zondag, G. B. & Hensgens, L. A. M. 2001. A simple screening method for transgenic rice tissue based on PCR. (online) http://www.gramene. org/newsletter/rice_genetics/rgn8/v8p 161.html (20 Jul. 2003).

McMaster, G. K. & Carmicheal, G. G. 1977. Analysis of single- and doublestranded nucleic acids on polyacrylamide and agarose gels by using glyoxal and acridine orange. *Proc. Natl. Acad. Sci. USA* 74(11): 4835-4838.

Mullet, J. E. 1993. Dynamic regulation of chloroplast transcription. *Plant Physiol.* 103: 309-313.

Nakamura, M., Tsunoda, T. & Obokata, J. 2002. Photosynthesis nuclear genes generally lack TATA-boxes: a tobacco photosystem I gene responds to light through an initiator. *Plant J* 29(1): 1-10.

Pastuglia, M., Roby, D., Dumas, C. & Cock, J. M. 1997. Rapid induction by wounding and bacterial infection of an S gene family receptor-like kinase gene in *Brassica oleracea. Plant Cell* 9: 49-60.

Rochester, D. E., Winer, J. A. & Shah, D. M. 1986. The structure and expression of maize genes encoding the major heat shock protein, hsp70. *EMBO J.* 5(3): 451-458.

Sambrook, J. & Russell, D. W. 2001. *Molecular cloning: a laboratory manual.* Third Ed. New York: Cold Spring Harbor Press.

Siti Nor Akmar Abdullah, Farida, H. S. & Cheah, S. C. 1995. Construction of oil palm mesocarp cDNA library and the isolation of mesocarp-specific cDNA clones. Asia Pacific Journal of Molecular Biology and Biotechnology. 3(2): 106-111.

Siti Nor Akmar Abdullah. 1999. Structure and regulation of stearoyl-ACP desaturase and metallothionien-like genes in developing fruits of oil palm. Ph.D Thesis. U.K.: University of East Anglia.

Stockinger, E. J. & Walling, L. L. 1994. A chlorophyll a/b binding gene from soybean (*Glycine max* [L.] Merr.). *Plant Physiol.* 104: 1475-1476.

Weigel, D. & Glazebrook, J. 2002. *Arabidopsis*: a laboratory manual. Cold Spring Harbor Laboratory Press, Cold Spring Harbor, N.Y.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of this invention.

The invention claimed is:

1. A nucleic acid construct comprising an isolated nucleic acid comprising the sequence of SEQ ID NO: 1 operably linked to a recombinant nucleic acid, wherein the nucleic acid construct when introduced into leaf tissues and/or photosynthetic tissues, stimulates expression of the recombinant nucleic acid in the leaf tissues and/or photosynthetic tissues, wherein the recombinant nucleic acid encodes a protein that imparts insect resistance, production of bioplastic, production of nutraceutical products, production of pharmaceutical macromolecules including therapeutic and diagnostic proteins, antibodies and vaccines, or results in an increase in photosynthetic rate of a plant.

2. A vector comprising a nucleic acid construct comprising an isolated nucleic acid comprising the sequence of SEQ ID NO: 1 operably linked to a recombinant nucleic acid, wherein the nucleic acid construct when introduced into leaf tissues and/or photosynthetic tissues, stimulates expression of the recombinant nucleic acid in the leaf tissues and/or photosynthetic tissues.

3. A cell comprising a nucleic acid construct comprising an isolated nucleic acid comprising the sequence of SEQ ID NO: 1 operably linked to a recombinant nucleic acid, wherein the nucleic acid construct when introduced into leaf tissues and/or photosynthetic tissues, stimulates expression of the recombinant nucleic acid in the leaf tissues and/or photosynthetic tissues.

4. A transgenic plant comprising a nucleic acid construct comprising an isolated nucleic acid comprising the sequence of SEQ ID NO: 1 operably linked to a recombinant nucleic acid, wherein the nucleic acid construct when introduced into leaf tissues and/or photosynthetic tissues, stimulates expression of the recombinant nucleic acid in the leaf tissues and/or photosynthetic tissues.

5. The transgenic plant of claim 4, wherein expression of the recombinant nucleic acid causes insect resistance, production of bioplastic, production of nutraceutical products, production of pharmaceutical macromolecules including therapeutic and diagnostic proteins, antibodies and vaccines, or results in an increase in photosynthetic rate of the plant.

6. A nucleic acid construct comprising a fragment of the nucleic acid of SEQ ID NO: 1 with promoter activity, wherein the fragment comprises the following elements depicted in FIG. 12: GATA I box, GATA II box, CCAAT box, and the G-box, operably linked to a recombinant nucleic acid, wherein the nucleic acid construct when introduced into leaf tissues and/or photosynthetic tissues, stimulates expression of the recombinant nucleic acid in the leaf tissues and/or photosynthetic tissues, wherein the recombinant nucleic acid encodes a protein that imparts insect resistance, production of bioplastic, production of nutraceutical products, production of pharmaceutical macromolecules including therapeutic and diagnostic proteins, antibodies and vaccines, or results in an increase in photosynthetic rate of a plant.

7. The nucleic acid construct of claim 6, wherein the fragment of the nucleic acid of SEQ ID NO:1 further comprises one or more promoter elements as depicted in FIG. 12 selected from the group consisting of: initiator element (Inr), I-box, wound responsive element (WUN), abscisic acid responsive element (ABA), and heat-shock responsive element (HSE).

8. A vector comprising a nucleic acid construct comprising a fragment of the nucleic acid of SEQ ID NO: 1 with promoter activity, wherein the fragment comprises the following elements depicted in FIG. 12: GATA I box, GATA II box, CCAAT box, and the G-box, operably linked to a recombinant nucleic acid, wherein the nucleic acid construct when introduced into leaf tissues and/or photosynthetic tissues, stimulates expression of the recombinant nucleic acid in the leaf tissues and/or photosynthetic tissues.

9. The vector of claim 8, wherein the fragment of the nucleic acid of SEQ ID NO:1 further comprises one or more promoter elements as depicted in FIG. 12 selected from the group consisting of: initiator element (Inr), I-box, wound responsive element (WUN), abscisic acid responsive element (ABA), and heat-shock responsive element (HSE).

10. A cell comprising a nucleic acid construct comprising a fragment of the nucleic acid of SEQ ID NO: 1 with promoter activity, wherein the fragment comprises the following elements depicted in FIG. 12: GATA I box, GATA II box, CCAAT box, and the G-box, operably linked to a recombinant nucleic acid, wherein the nucleic acid construct when introduced into leaf tissues and/or photosynthetic tissues, stimulates expression of the recombinant nucleic acid in the leaf tissues and/or photosynthetic tissues.

11. The cell of claim 10, wherein the fragment of the nucleic acid of SEQ ID NO:1 further comprises one or more promoter elements as depicted in FIG. 12 selected from the group consisting of: initiator element (Inr), I-box, wound responsive element (WUN), abscisic acid responsive element (ABA), and heat-shock responsive element (HSE).

12. A transgenic plant comprising a nucleic acid construct comprising a fragment of the nucleic acid of SEQ ID NO: 1 with promoter activity, wherein the fragment comprises the following elements depicted in FIG. 12: GATA I box, GATA II box, CCAAT box, and the G-box, operably linked to a recombinant nucleic acid, wherein the nucleic acid construct when introduced into leaf tissues and/or photosynthetic tissues, stimulates expression of the recombinant nucleic acid in the leaf tissues and/or photosynthetic tissues.

13. The transgenic plant of claim 12, wherein the fragment of the nucleic acid of SEQ ID NO:1 further comprises one or more promoter elements as depicted in FIG. 12 selected from the group consisting of: initiator element (Inr), I-box, wound responsive element (WUN), abscisic acid responsive element (ABA), and heat-shock responsive element (HSE).

14. The transgenic plant of claim 12, wherein expression of the recombinant nucleic acid causes insect resistance, production of bioplastic, production of nutraceutical products, production of pharmaceutical macromolecules including therapeutic and diagnostic proteins, antibodies and vaccines, or results in an increase in photosynthetic rate of the plant.

15. The transgenic plant of claim 13, wherein expression of the recombinant nucleic acid causes insect resistance, production of bioplastic, production of nutraceutical products, production of pharmaceutical macromolecules including therapeutic and diagnostic proteins, antibodies and vaccines, or results in an increase in photosynthetic rate of the plant.

* * * * *